(12) United States Patent
Harrison et al.

(10) Patent No.: US 9,950,060 B2
(45) Date of Patent: Apr. 24, 2018

(54) BIOCHEMICALLY STABILIZED HIV-1 ENV TRIMER VACCINE

(71) Applicants: Beth Israel Deaconess Medical Center, Boston, MA (US); Children's Medical Center Corporation, Boston, MA (US)

(72) Inventors: Stephen C. Harrison, Brighton, MA (US); Bing Chen, Chestnut Hill, MA (US); Dan H. Barouch, Boston, MA (US); Joseph P. Nkoloa, Watertown, MA (US); Michael Scott Seaman, West Roxbury, MA (US)

(73) Assignees: Beth Israel Deaconess Medical Center, Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/596,312

(22) Filed: May 16, 2017

(65) Prior Publication Data

US 2017/0290907 A1    Oct. 12, 2017

Related U.S. Application Data

(63) Continuation of application No. 13/082,601, filed on Apr. 8, 2011, now Pat. No. 9,707,289, which is a continuation of application No. PCT/US2009/060494, filed on Oct. 13, 2009.

(60) Provisional application No. 61/104,449, filed on Oct. 10, 2008.

(51) Int. Cl.

| | | |
|---|---|---|
| *A61K 39/00* | (2006.01) | |
| *G01N 33/569* | (2006.01) | |
| *C07K 14/29* | (2006.01) | |
| *A61K 39/02* | (2006.01) | |
| *C07K 16/12* | (2006.01) | |
| *A61K 39/21* | (2006.01) | |
| *C07K 14/005* | (2006.01) | |
| *C12N 7/00* | (2006.01) | |

(52) U.S. Cl.
CPC ............ *A61K 39/21* (2013.01); *C07K 14/005* (2013.01); *C12N 7/00* (2013.01); *A61K 2039/53* (2013.01); *C12N 2740/16051* (2013.01); *C12N 2740/16122* (2013.01); *C12N 2740/16134* (2013.01); *C12N 2740/16171* (2013.01)

(58) Field of Classification Search
CPC ............ A61K 39/00; G01N 33/56911; G01N 2333/195; G01N 2469/10; C07K 14/29
See application file for complete search history.

(56) References Cited

U.S. PATENT DOCUMENTS

| | | |
|---|---|---|
| 4,603,112 A | 7/1986 | Paoletti et al. |
| 5,639,649 A | 6/1997 | Almond et al. |
| 5,643,576 A | 7/1997 | Johnston et al. |
| 6,911,205 B2 | 6/2005 | Sodroski et al. |
| 7,592,014 B2 | 9/2009 | Binley et al. |
| 7,901,690 B2 | 3/2011 | Lu et al. |
| 7,939,083 B2 | 5/2011 | Dey et al. |
| 9,017,691 B2 | 4/2015 | Barouch et al. |
| 2007/0298051 A1 | 12/2007 | Barouch et al. |
| 2011/0250220 A1 | 10/2011 | Dey et al. |
| 2012/0045472 A1 | 2/2012 | Harrison et al. |
| 2013/0189754 A1 | 7/2013 | Parks et al. |
| 2014/0302080 A1 | 10/2014 | Barouch et al. |
| 2014/0348791 A1 | 11/2014 | Barouch et al. |
| 2015/0291935 A1 | 10/2015 | Barouch et al. |
| 2016/0024156 A1 | 1/2016 | Barouch et al. |

FOREIGN PATENT DOCUMENTS

| | | |
|---|---|---|
| CN | 102282175 A | 12/2011 |
| WO | 0119958 | 3/2001 |
| WO | 2004/0044155 | 5/2004 |
| WO | 2006002079 | 1/2006 |
| WO | 2006020071 | 2/2006 |
| WO | 2006/040330 | 4/2006 |
| WO | 2007005934 | 1/2007 |
| WO | 2007/024941 | 3/2007 |
| WO | 2007/104792 | 9/2007 |
| WO | 2007/149491 | 12/2007 |
| WO | 2008063331 | 5/2008 |
| WO | 2010/042942 A2 | 4/2010 |
| WO | 2010/059732 | 5/2010 |
| WO | 2012/030904 | 3/2012 |
| WO | 2013055908 | 4/2013 |

(Continued)

OTHER PUBLICATIONS

Rodenburg et al. "Near full-length clones and reference sequences for subtype C isolates of HIV type 1 from three different continents", AID Research and Human Retroviruses, 17(2), 2001:161-168.*

Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).

Gray et al, "Safety and Efficacy of the HVTN 503/Phambili Study: A Double-Blind Randomized Placebo-Controlled Test-of-Concept Study of a Clade-B-Based HIV-1 Vaccine in South Africa," Lancet Infectious Diseases, vol. 11, No. 7, pp. 507-515 (Jul. 2011).

(Continued)

*Primary Examiner* — Barry A Chestnut
(74) *Attorney, Agent, or Firm* — Panitch Schwarze Belisario & Nadel LLP

(57) ABSTRACT

Stabilized trimers of a clade A strain and a clade C strain of HIV-1 are provided. Broadly neutralizing antisera against HIV-1, methods of making broadly neutralizing antisera against HIV-1, broadly neutralizing vaccines against HIV-1, as well as methods of treating subjects infected with HIV, preventing HIV infection, and inhibiting HIV-mediated activities are also provided.

22 Claims, 17 Drawing Sheets

(56) References Cited

FOREIGN PATENT DOCUMENTS

| WO | 2014/047261 | 3/2014 |
|---|---|---|
| WO | 2015/048770 | 4/2015 |

OTHER PUBLICATIONS

Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Georgiev et al, "Delineating Antibody Recognition in Polyclonal Sera from Patterns of HIV-1 Isolate Neutralization," Science, vol. 340, No. 6133, pp. 751-756 (2013).
GenBank Accession No. KC769514. Retrieved on Dec. 30, 2014 (2 pages).
Genbank Accession No. AF286227.1, "HIV-1 strain 97Za012 from South Africa, complete genome." Accessed Jan. 6, 2016.
Gaschen et al, "Diversity Consideration in HIV-1 Vaccine Selection," Science, vol. 296, No. 5577, pp. 2354-2360 (Jun. 28, 2002).
Gao et al., "A Comprehensive Panel of Near-Full-Length Clones and Reference Sequencesfor Non-Subtype B Isolates of Human Immunodeficiency Virus Type 1,"Journal of Virology, vol. 72, No. 7, pp. 5680-5698 (1998).
Gao et al, "Molecular Cloning and Analysis of Functional Envelope Genes from Human Immunodeficiency Virus Type 1 Sequence Subtypes A through G" Journal of Virology, vol. 70, No. 3, pp. 1651-1667 (Mar. 1996).
Gao et al, "Centralized HIV-1 Envelope Immunogens and Neutralizing Antibodies," Current HIV Research, vol. 5, No. 6, pp. 572-577 (2007).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gallo, et al., "The HIV Env-mediated Fusion Reaction," Biochemics et Biophysica Acta, pp. 36-50 (2003).
Gallo, "The End or the Beginning of the Drive to an HIV-Preventive Vaccine: A View from over 20 Years", The Lancet, vol. 366, No. 9500, pp. 1894-1898 (Nov. 2005).
Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).
Frey et al, "A Fusion-Intermediate State of HIV-1 gp41 Targeted by Broadly Neutralizing Antibodies," Proceedings of the National Academy of Sciences of the United States of America, vol. 105, No. 10, pp. 3739-3744 (Mar. 11, 2008).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Flynn, et al., "Placebo-Controlled Phase 3 Trial of a Recombinant Glycoprotein 120 Vaccine to Prevent HIV-1 Infection," J. Infect. Dis., vol. 191, pp. 654-665 (2005).
Fischer et al, "Polyvalent Vaccines for Optimal Coverage of Potential T-Cell Epitopes in Global HIV-1 Variants," Nature Medicine, vol. 13, No. 1, pp. 100-106 (2007).
Fischer et al, "Identification of a Peptide Mimicking the Binding Pattern of an Antiphospholipid Antibody," Immunobiology, vol. 211, No. 9, pp. 695-699 (2006).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Examination Report dated Jan. 5, 2015 in AU Application No. 2009303284.
European Office Action for Application No. 09820044.7, dated Jan. 12, 2016.
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).
Dey, et al., "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).
Desrosiers, "Prospects for an AIDS Vaccine", Nature Medicine, vol. 10, No. 3, pp. 221-223 (2004).
Derby, et al., "Isolation and Characterization of Monoclonal Antibodies Elicited by Trimeric HIV-1 ENV gp140 Protein 14 Immunogens," Virology 366, pp. 433-445 (2007).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
Crooks, et al., "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Cohen, "Naked DNA Points Way to Vaccines," Science, vol. 259, pp. 1691-1692 (Mar. 1993).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Chen et al, "A Chimeric Protein of Simian Immunodeficiency Virus Envelope Glycoprotein gp140 and *Escherichia coli* Aspartate Transcarbamoylase," Journal of Virology, vol. 78, No. 9, pp. 4508-4516 (May 2004).
Checkley et al, "HIV-1 Envelope Glycoprotein Biosynthesis, Trafficking, and Incorporation," Journal of Molecular Biology, vol. 410, No. 4, pp. 582-608 (2011).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Carrow, et al., "High Prevalance of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Calarese et al, "Antibody Domain Exchange is an Immunological Solution to Carbohydrate Cluster Recognition," Science, vol. 300, No. 5628, pp. 2065-2071 (2003).

(56) References Cited

OTHER PUBLICATIONS

Burton, et al., "HIV Vaccine Design and the Neutralizing Antibody Problem," Nature Immunology, vol. 5, No. 3, pp. 233-236 (Mar. 2004).
Burke et al, "Neutralizing Antibody Responses to Subtype B and C Adjuvanted HIV Envelope Protein Vaccination in Rabbits," Virology, vol. 387, pp. 147-155 (2009).
Buchbinder et al, "Efficacy Assessment of a Cell-Mediated Immunity HIV-1 Vaccine (The Step Study): A Double-Bind, Randomised, Placebo-Controlled, Test-of-Concept Trial," Lancet, vol. 372, No. 9653, pp. 1881-1893 (Nov. 29, 2008).
Bower, et al., "HIV-1 ENV gp 140 Trimers Elicit Neutralizing Antibodies Without Efficient Induction of Conformational Antibodies," Vaccine 24, 5442-5451 (2006).
Bower et al., "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).
Binley, et al., "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Berman, et al., "Comparison of the Immune Response to Recombinant gp120 in Humans and Chimpanzees," AIDS, vol. 8, pp. 591-601 (1994).
Berger, et al., "Chemokine Receptors as HIV-1 Coreceptors: Roles in Viral Entry, Tropism and Disease," Annu. Rev. Immunol., vol. 17, pp. 657-700 (1999).
Beddows, et al., "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric p120," Virology, vol. 360, pp. 329-340 (2007).
Barouch et al, "Mosaic HIV-1 Vaccines Expand the Breadth and Depth of Cellular Immune Responses in Rhesus Monkeys," Nature Medicine, vol. 16, No. 3, pp. 319-323 (Mar. 2010).
Barouch "Challenges in the Development of an HIV-1 Vaccine," Nature, vol. 455, pp. 613-619 (Oct. 2008).
Barnett et al., "Development of V2-deleted trimeric envelope vaccine candidates from human immunodeficiency virus type 1 (HIV-1) subtypes Band C," Microbes Infect., vol. 7, vol. 14, pp. 1386-1391 (2005).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Amanna et al, "Contributions of Humoral and Cellular Immunity to Vaccine-Induced Protection in Humans," Virology, vol. 411, No. 2, pp. 206-215 (2011).
Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Abbink, et al., "Comparative Seroprevalence and Immunogenicity of Six Rare Serotype Recombinant Adenovirus Vaccine Vectors from Subgroups Band D," Journal of Virology, vol. 81, No. 9, pp. 4654-4663 (May 2007).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
Page, et al., "Studies on the Immunogenicity of Chinese Hamster Ovary Cell-Derived Recombinant gp120 (HIV-1111B)," Vaccine, vol. 9, pp. 47-52 (Jan. 1991).

Office Action dated May 16, 2014 in EP Application No. 09820044.7.
Ofek et al, "Structure and Mechanistic Analysis of the Anti-Human Immunodeficiency Virus Type 1 Antibody 2F5 in Complex with its gp41 Epitope," Journal of Virology, vol. 78, No. 19, pp. 10724-10737 (Oct. 2004).
Nkolola et al, "Characterization and Immunogenicily of a Novel Mosaic M HIV-1 gp140 Trimer," Journal of Virology, vol. 88, No. 17, pp. 9538-9552 (2014).
Nkolola et al, "Breadth of Neutralizing Antibodies Elicited by Stable, Homogenous Clade and Clade C HIV-1 gp140 Envelope Trimers in Guinea Pigs," Journal of Virology, vol. 84, No. 7, pp. 3270-3279 (Apr. 2010).
Nara, et al., "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).
Morner, et al., "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Montefiori, "Measuring HIV Neutralization in a Luciferase Reporter Gene Assay," HIV Protocols Second 25 Edition, vol. 485, pp. 395-405 (2009).
Montefiori, "Evaluating Neutralizing Antibodies Against HIV, SIV, and SHIV in Luciferase Reporter Gene Assays," Current Protocols in Immunology, vol. 12, No. 11, pp. 1-17 (2004).
Montefiori et al, "Antibody-Based HIV-1 Vaccines: Recent Developments and Future Directions," PLOS Medicine, vol. 4, No. 12, pp. e348 (2007).
McLellan et al, "Structure of HIV-1 gp120 V1/V2 Domain with Broadly Neutralizing Antibody PG9," Nature, vol. 480, No. 7377, pp. 336-343 (2011).
McGuire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).
McElrath et al, "Induction of Immunity to Human Immunodeficiency Virus Type-1 by Vaccination," Immunity, vol. 33, pp. 542-554 (Oct. 29, 2010).
McCoy et al, "Potent and Broad Neutralization of HIV-1 by a Llama Antibody Elicited by Immunization," The Journal of Experimental Medicine, vol. 209, No. 6, pp. 1091-1103 (2012).
McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).
McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).
Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).
Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).
Mangeat et al, "Lentiviral Vectors and Antiretroviral Intrinsic Immunity," Human Gene Therapy, vol. 16, No. 8, pp. 913-920 (Aug. 2005).
Malherbe et al, "Sequential Immunization with a Subtype B HIV-1 Envelope *Quasi*species Partially Mimics the In Vivo Development of Neutralizing Antibodies," Journal of Virology, vol. 85, No. 11, pp. 5262-5274 (Jun. 2011).
Lynch et al, "The Development of CD4 Binding Site Antibodies During HIV-1 Infection," Journal of Virology, vol. 86, No. 14, pp. 7588-7595 (Jul. 2012).

(56) References Cited

OTHER PUBLICATIONS

Li, et al., "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Li, et al., "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).

Lin et al, "Designing Immunogens to Elicit Broadly Neutralizing Antibodies to the HIV-1 Envelope Glycoprotein," Current HIV Research, vol. 5, No. 6, pp. 514-541 (2007)

Liao et al, "Co-Evolution of a Broadly Neutralizing HIV-1 Antibody and Founder Virus," Nature, vol. 496, No. 7446, pp. 469-476 (Apr. 25, 2013).

Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).

Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).

Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).

Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).

Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).

Li et al, "Broad HIV-1 Neutralization Mediated by CD4-Binding Site Antibodies," Nature Medicine, vol. 13, No. 9, pp. 1032-1039 (Sep. 2007).

Levine, Why Do We Not Yet Have a Human Immunodeficiency Virus Vaccine, J. Virol., vol. 82, No. 24, pp. 11998-12000 (Dec. 2008).

Lee et al, "A Single Point Mutation in HIV-1 V3 Loop Alters the Immunogenic Properties of rgp120," Archives of Virology, vol. 145, pp. 2087-2103 (2000).

Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).

Kovacs et al, "HIV-1 Envelope Trimer Elicits More Potent Neutralizing Antibody Responses than Monomeric gp120," Proceedings of the National Academy of Sciences of the United States of America, vol. 109, No. 30, pp. 12111-12116 (Jul. 24, 2012).

Kothe et al, "Antigenicity and Immunogenicity of HIV-1 Consensus Subtype B Envelope Glycoproteins," Virology, vol. 360, No. 1, pp. 218-234 (Mar. 30, 2007).

Kothe et al, "Ancestral and Consensus Envelope Immunogens for HIV-1 Subtype C," Virology, vol. 352, No. 2, pp. 438-449 (2006).

Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).

Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).

Kang, et al., "Structural and Immunogenicity Studies of a Cleaved, Stabilized Envelope Trimer Derived from Subtype A HIV-1," Vaccine 27, pp. 5120-5132 (2009).

Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).

Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).

Jeffs et al, "Expression and Characterization of Recombinant Oligomeric Envelope Glycoproteins Derived From Primary Isolates of HIV-1," Vaccine, vol. 22, No. 8, pp. 1032-1046 (2004).

Huang et al, "Broad and Potent Neutralization of HIV-1 by a gp41-Specific Human Antibody," Nature, vol. 491, No. 7424, pp. 406-412 (2012).

Haynes et al, "Immune-Correlates Analysis of an HIV-1 Vaccine Efficacy Trial," The New England Journal of Medicine, vol. 366, No. 14, pp. 1275-1286 (Apr. 5, 2012).

Hammer et al, "Efficacy Trial of a DNA/rAd5 HIV-1 Preventive Vaccine," The New England Journal of Medicine, vol. 369, No. 22, pp. 2083-2092 (Nov. 28, 2013).

Zolla-Pazner, et al., "Focusing the Immune Response on the V3 Loop, a Neutralizing Epitope of the HIV-1 gp210 Envelope," Virology, vol. 372, pp. 233-246 (2008).

Zhou et al, "Structural Basis for Broad and Potent Neutralization of HIV-1 by Antibody VRC01," Science, vol. 329, No. 5993, pp. 811-817 (Aug. 13, 2010).

Zhang, et al., "Expression, Purification, and Characterization of Recombinant HIV gp140. The gp41 Ectodomain of HIV or Simian Immunodeficiency Virus is Sufficient to Maintain the Retroviral Envelope Glycoprotein as a Trimer," The Journal of Biological Chemistry, vol. 276, No. 43, pp. 39577-39585 (Oct. 26, 2001).

Zhang et al., Extensively Cross-Reactive Anti-HIV-1 Neutralizing Antibodies Induced by gp140 Immunization, PNAS, vol. 104, No. 24, pp. 10193-10198 (2007).

Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).

Yang, Xinzhen et al., "Modifications That Stabilize Human Immunodeficiency Virus Envelope Glycoprotein Trimers in Solution," Journal of Virology, vol. 74(10):4746-4754 {2000).

Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).

Yang et al, "Highly Stable Trimers Formed by Human Immunodeficiency Virus Type 1 Envelope Glycoproteins Fused with the Trimeric Motif of T4 Bacteriophage Fibritin," Journal of Virology, vol. 76, No. 9, pp. 4634-4642 (May 2002).

Wyatt et al., "The Antigenic Structure of the HIV gp120 Envelope Glycoprotein," Nature, vol. 393, pp. 705-711 (Jun. 18, 1998).

Wu et al, "Rational Design of Envelope Identifies Broadly Neutralizing Human Monoclonal Antibodies to HIV-1," Science, vol. 329, No. 5993, pp. 856-861 (Aug. 13, 2010).

Wiznerowicz et al, "Harnessing HIV for Therapy, Basic Research and Biotechnology," Trends in Biotechnology, vol. 23, No. 1, pp. 42-47 (Jan. 2005).

Wattanapitayakul et al, "Recent Developments in Gene Therapy for Cardiac Disease," Biomed & Pharmacother, vol. 54, No. 1, pp. 487-504 (2000).

Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).

Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).

(56) References Cited

OTHER PUBLICATIONS

Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Walker, et al., "Broad and Potent Neutralizing Antibodies from an African Donor Reveal a New HIV-1 Vaccine D Target," Science, vol. 326, Oct. 9, 2009.
Walker et al, "Toward an AIDS Vaccine," Science, vol. 320, pp. 760-764 (May 9, 2008).
Walker et al, "Broad Neutralization Coverage of HIV by Multiple Highly Potent Antibodies," Nature, vol. 477, No. 7365, pp. 466-470 (Sep. 22, 2011).
Walker et al, "Broad and Potent Neutralizing Antibodies from an African Donor Reveal a New HIV-1 Vaccine Target," Science, vol. 326, No. 5950, pp. 285-289 (Oct. 9, 2009).
Vogel, et al., "The Majority of Neutralizing Abs in HIV-1-Infected Patients Recognize Linear V3 Loop Sequences," The Journal of Immunology, vol. 153, pp. 1895-1904 (1994).
Vaine, et al., "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vaine et al,"Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Summons to Attend Oral Proceedings dated Apr. 11, 2017 in EP Application No. 09820044.7.
Stamatos et al, "Neutralizing Antibodies Generated During Natural HIV-1 Infection: Good News for an HIV-1 Vaccine?," Nature Medicine, vol. 15, No. 8, pp. 866-870 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Seaman et al, "Standardized Assessment of NAb Responses Elicited in Rhesus Monkeys Immunized with Single- or Multi-Glade HIV-1 Envelope Immunogens," Virology, vol. 367, pp. 175-186 (2007).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Scheid, et al., "Broad Diversity of Neutralizing Antibodies Isolated From Memory B Cells in HIV-Infected Individuals," D Nature, vol. 458, pp. 636-640 (Apr. 2, 2009).
Scheid et al, "Sequence and Structural Convergence of Broad and Potent HIV Antibodies That Mimic CD4 Binding," Science, vol. 333, pp. 1633-1637 (2011).

Sattentau, "Envelope Glycoprotein Trimers as HIV-1 Vaccine Immunogens", Vaccines, vol. 1, pp. 497-512 (2013).
Saphire et al, "Crystal Structure of a Neutralizing Human IgG Against HIV-1: A Template for Vaccine Design," Science, vol. 293, No. 5532, pp. 1155-1159 (2001).
Santra et al, "Mosaic Vaccines Elicit CD8+ T Lymphocyte Responses in Monkeys that Confer Enhanced Immune Coverage of Diverse HIV Strains," Nature Medicine, vol. 16, No. 3, pp. 324-328 (Mar. 2010).
Salminen et al., "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).
Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Rerks-Ngarm et al, "Vaccination with ALVAC and AIDSVAX to Prevent HIV-1 Infection in Thailand," The New England Journal of Medicine, vol. 361, No. 23, pp. 222-233 (Dec. 3, 2009).
Polonis et al. "Recent Advances in the Characterization of HIV-1 Neutralization Assays for Standardized Evaluation of the Antibody Response to Infection and Vaccination," Virology, 375, pp. 315-320 (2008).
Plotkin, "The RV144 Thai HIV Vaccine Trial," Human Vaccines, vol. 6, No. 2, p. 159 (Feb. 2010).
Plotkin, "Immunologic Correlates of Protection Induced by Vaccination," Pediatric Infectious Disease Journal, vol. 20, No. 1, pp. 63-75 (2001).
Plotkin, "Correlates of Protection Induced by Vaccination," Clinical and Vaccine Immunology, vol. 17, No. 7, pp. 1055-1065 (Jul. 2010).
Plotkin et al, "Postscript Relating to New Allegations Made by Edward Hooper at the Royal Society Discussion Meeting on Sep. 11, 2000," Philosophical Transactions of the Royal Society of London B: Biological Sciences, vol. 356, No. 1410, pp. 825-829 (2001).
Pitisuttithum, et al., "Randomized, Double-Bind, Placebo-Controlled Efficacy Trial of a Bivalent Recombinant Glycoprotein 120 HIV-1 Vaccine Among Injection Drug Users in Bangkok, Thailand," The Journal of Infectious Diseases, vol. 194, pp. 1661-1671 (2006).
Pinter, "Roles of HIV-1 Env Variable Regions in Viral Neutralization and Vaccine Development," Current HIV Research, vol. 5, No. 6, pp. 542-553 (2007).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).
Pejchal et al, "A Potent and Broad Neutralizing Antibody Recognizes and Penetrates the HIV Glycan Shield," Science, vol. 334, No. 6059, pp. 1097-1103 (2011).
PCT/US2009/060494 Written Opinion and International Search Report.
PCT/US2009/060494 International Preliminary Report on Patentability.
Pantophlet, et al., "GP120: Target for Neutralizing HIV-1 Antibodies," Annu. Rev. Immunol., vol. 24, pp. 739-769 (2006).
Nkolola et al, "Stability and Neutralization Capacity of a Novel Mosaic HIV-1 gp140 trimer in a Guinea Pig Model" AIDS Vaccine Poster, Ragan Institute, 1 pg. (2012).
Nkolola et al, "Stability and neutralization capacity of a novel mosaic HIV-1 gp140 trimer in a guinea pig model," Retrovirology, vol. 9, Supp. 2, pp. 299 (2012).
Office Action dated Sep. 26, 2017 in JP Application No. 2015-551842.

\* cited by examiner

```
92UG037.8 V1    SYNITNNITNSITNSSVNMREEIK (SEQ ID NO:3)
CZA97.012 V1    TNATFKNVTNDMNKEIR (SEQ ID NO:4)

92UG037.8 V2    SFNMTTELRDKNRKVYSLFYKLDVVQIN-NGNNSSNL-YRLIN
                                                        (SEQ ID NO:5)
CZA97.012 V2    SFNTTTEIRDKKQQGYALFYRPDIVLLKENRNNSNNSEYILIN
                                                        (SEQ ID NO:6)

92UG037.8 V3    TRPNNNTRKSVRIGPGQTFYATGDIIGDIRQAH (SEQ ID NO:7)
CZA97.012 V3    TRPNNNTRKSMRIGPGQTFYATGDIIGDIRQAY (SEQ ID NO:8)
```

| | | | Tier 1 Serum NAb Titers (ID50) | | | | | | Control |
|---|---|---|---|---|---|---|---|---|---|
| Trimer | Animal # | Timepoint | Tier 1 C MW965.26 | Tier 1 A DJ263.8 | Tier 1 B SF162.LS | Tier 1 B BaL.26 | Vaccine 92UG037.8 | Vaccine CZA97.012 | MuLV |
| Clade A gp140 | 1 | Pre | 85 | 58 | <20 | 64 | 32 | 24 | 23 |
| | | Post | 18,618 | 2,109 | 895 | 32 | 24 | 39 | <20 |
| | 2 | Pre | 93 | 58 | 51 | 84 | 33 | <20 | <20 |
| | | Post | 20,310 | 1,622 | 242 | 52 | 35 | 33 | 32 |
| | 3 | Pre | 54 | 48 | <20 | 41 | 24 | 72 | <20 |
| | | Post | 17,902 | 2,143 | 782 | 84 | 55 | 77 | 30 |
| | 4 | Pre | 62 | 46 | 23 | 26 | 32 | 46 | <20 |
| | | Post | 22,876 | 1,474 | 820 | 48 | 42 | 102 | 29 |
| | 5 | Pre | 36 | 46 | <20 | 32 | 23 | 72 | <20 |
| | | Post | 22,461 | 4,121 | 4,450 | 99 | 40 | 30 | 25 |
| Clade C gp140 | 6 | Pre | 36 | 35 | <20 | 37 | 26 | 54 | <20 |
| | | Post | 33,847 | 1,813 | 610 | 67 | 54 | 52 | 84 |
| | 7 | Pre | 63 | 35 | 20 | 39 | 42 | 68 | 34 |
| | | Post | 20,654 | 2,211 | 544 | 89 | 46 | 39 | 31 |
| | 8 | Pre | 31 | <20 | <20 | 22 | <20 | <20 | 24 |
| | | Post | 16,260 | 703 | 678 | 48 | 60 | 40 | 36 |
| | 9 | Pre | 96 | 43 | 43 | 74 | 28 | <20 | 24 |
| | | Post | 14,274 | 883 | 1,195 | 53 | 64 | 42 | 57 |
| | 10 | Pre | 22 | <20 | <20 | <20 | 33 | 30 | 25 |
| | | Post | 23,726 | 1,291 | 1,089 | 207 | 90 | 42 | 42 |

| | | | Tier 2 Clade A Serum NAb Titers (ID50) | | | | | | Control |
|---|---|---|---|---|---|---|---|---|---|
| Trimer | Animal # | Timepoint | Tier 2 A Q769.d22 | Tier 2 A Q168.a2 | Tier 2 A Q842.d12 | Tier 2 A 3718.v3 | Tier 2 A 0330.v4 | Tier 2 A 0439.v5 | MuLV |
| Clade A gp140 | 1 | Pre | 20 | 23 | 23 | 30 | 26 | 35 | 23 |
| | | Post | <20 | <20 | <20 | 23 | 31 | 33 | <20 |
| | 2 | Pre | <20 | 22 | 21 | <20 | 21 | 28 | <20 |
| | | Post | 40 | 40 | <20 | 39 | 23 | 51 | 32 |
| | 3 | Pre | 41 | 27 | 35 | 24 | 21 | 34 | <20 |
| | | Post | 41 | 61 | 55 | 99 | 83 | 193 | 30 |
| | 4 | Pre | 23 | 23 | 27 | <20 | <20 | 20 | <20 |
| | | Post | 41 | 22 | 33 | 64 | 39 | 52 | 29 |
| | 5 | Pre | <20 | 27 | 32 | 23 | 31 | <20 | <20 |
| | | Post | 42 | 38 | 39 | 58 | 35 | 59 | 25 |
| Clade C gp140 | 6 | Pre | 27 | 29 | 23 | <20 | <20 | <20 | <20 |
| | | Post | 65 | 51 | 58 | 80 | 65 | 81 | 84 |
| | 7 | Pre | 29 | 27 | 29 | 36 | 55 | 35 | 34 |
| | | Post | 39 | 38 | 40 | 63 | 42 | 60 | 31 |
| | 8 | Pre | <20 | <20 | <20 | <20 | <20 | <20 | 24 |
| | | Post | 111 | 108 | 121 | 686 | 389 | 1,602 | 36 |
| | 9 | Pre | <20 | <20 | 25 | 28 | 37 | 35 | 24 |
| | | Post | 48 | 46 | 59 | 75 | 58 | 81 | 57 |
| | 10 | Pre | <20 | <20 | <20 | <20 | 21 | <20 | 25 |
| | | Post | 62 | 50 | 56 | 85 | 74 | 110 | 42 |

Fig. 6

| | | | Tier 2 Clade B Serum NAb Titers (ID50) | | | | | | |
|---|---|---|---|---|---|---|---|---|---|
| Trimer | Animal # | Timepoint | Tier 2 B WITO4160.33 | Tier 2 B AC10.0.29 | Tier 2 B REJO451 | Tier 2 B 6535.3 | Tier 2 B SC422661 | Tier 2 B TRO.11 | Control MuLV |
| Clade A gp140 | 1 | Pre | 79 | 31 | 62 | 34 | 25 | 27 | 23 |
| | | Post | <20 | <20 | <20 | <20 | <20 | <20 | <20 |
| | 2 | Pre | 34 | 47 | 45 | 23 | 28 | 22 | <20 |
| | | Post | <20 | 35 | 39 | 22 | <20 | <20 | 32 |
| | 3 | Pre | 36 | 46 | 54 | 43 | 33 | 28 | <20 |
| | | Post | 75 | 79 | 50 | 74 | 69 | 26 | 30 |
| | 4 | Pre | <20 | <20 | <20 | <20 | <20 | <20 | <20 |
| | | Post | 26 | <20 | 33 | <20 | 32 | 21 | 29 |
| | 5 | Pre | <20 | 21 | 24 | <20 | 23 | <20 | <20 |
| | | Post | 41 | 161 | 40 | 152 | 42 | 30 | 25 |
| Clade C gp140 | 6 | Pre | <20 | <20 | <20 | <20 | <20 | <20 | <20 |
| | | Post | 147 | 218 | 156 | 80 | 140 | 91 | 84 |
| | 7 | Pre | 35 | 42 | 47 | 25 | 27 | 25 | 34 |
| | | Post | 36 | 49 | 37 | 28 | 32 | 20 | 31 |
| | 8 | Pre | <20 | 24 | <20 | <20 | <20 | <20 | 24 |
| | | Post | 71 | 105 | 66 | 78 | 76 | 63 | 36 |
| | 9 | Pre | 32 | 53 | 34 | 30 | 29 | 29 | 24 |
| | | Post | 57 | 131 | 55 | 109 | 115 | 65 | 57 |
| | 10 | Pre | 85 | 67 | 54 | <20 | 24 | <20 | 25 |
| | | Post | 105 | 1,219 | 110 | 55 | 59 | 47 | 42 |
| | | | Tier 2 Clade C Serum NAb Titers (ID50) | | | | | | |
| Trimer | Animal # | Timepoint | Tier 2 C ZM109F.PB4 | Tier 2 C ZM249M | Tier 2 C CAP45.2 | Tier 2 C Du123.6 | Tier 2 C Du422.1 | Tier 2 C ZM197M | Control MuLV |
| Clade A gp140 | 1 | Pre | 48 | 24 | <20 | <20 | 35 | 57 | 23 |
| | | Post | 106 | 30 | <20 | <20 | 22 | 35 | <20 |
| | 2 | Pre | 26 | 21 | <20 | <20 | 28 | 55 | <20 |
| | | Post | 121 | 36 | 31 | 33 | 35 | 47 | 32 |
| | 3 | Pre | 34 | <20 | <20 | <20 | 37 | 45 | <20 |
| | | Post | 360 | 268 | 213 | 51 | 67 | 138 | 30 |
| | 4 | Pre | <20 | <20 | <20 | 24 | 38 | 56 | <20 |
| | | Post | 131 | 52 | 61 | 35 | 48 | 95 | 29 |
| | 5 | Pre | <20 | <20 | <20 | <20 | 33 | 40 | <20 |
| | | Post | 182 | 59 | 69 | 41 | 50 | 86 | 25 |
| Clade C gp140 | 6 | Pre | <20 | <20 | <20 | 24 | 24 | 40 | <20 |
| | | Post | 146 | 108 | 170 | 55 | 73 | 159 | 84 |
| | 7 | Pre | 50 | 33 | 28 | <20 | 39 | 41 | 34 |
| | | Post | 140 | 59 | 118 | 45 | 45 | 101 | 31 |
| | 8 | Pre | <20 | <20 | <20 | <20 | <20 | <20 | 24 |
| | | Post | 933 | 884 | 584 | 38 | 32 | 73 | 36 |
| | 9 | Pre | 46 | 24 | 42 | <20 | 38 | 55 | 24 |
| | | Post | 173 | 75 | 140 | 52 | 100 | 142 | 57 |
| | 10 | Pre | <20 | <20 | <20 | <20 | <20 | 55 | 25 |
| | | Post | 203 | 100 | 188 | 79 | 103 | 239 | 42 |

Fig. 6 (Cont.)

| Trimer Immunogen | Tier 2 Virus Panel | % Positive |
|---|---|---|
| Clade A gp140 | Clade A | (4/30) 13% |
| | Clade B | (2/30) 7% |
| | Clade C | (8/30) 27% |
| Clade C gp140 | Clade A | (8/30) 27% |
| | Clade B | (6/30) 20% |
| | Clade C | (14/30) 47% |

Fig. 7

| Trimer | Animal # | Tier 1C MW965.26 | Tier 1A DJ263.8 | Tier 1B SF162.LS | Tier 2C ZM197M.PB7 | Tier 2C ZM109F.PB4 | Tier 2C CAP45.2.00.G3 | Tier 2A 0439.v5.c1 | Tier 2A 3718.v3.c11 | Tier 2B AC10.0.29 | Tier 2B 6535.3 |
|---|---|---|---|---|---|---|---|---|---|---|---|
| Clade A gp140 | 1 | 0.2 | 2.0 | 16.6 | >500 | 96 | >500 | >500 | >500 | >500 | 159 |
| | 2 | 0.1 | 2.5 | 26.5 | >500 | 89 | >500 | >500 | >500 | >500 | 178 |
| | 3 | 0.1 | 2.7 | 31.4 | >250 | 132 | >1,000 | >1,000 | >250 | >500 | 143 |
| | 4 | 0.3 | 7.1 | 21.6 | >1,000 | 178 | >1,000 | >1,000 | >1,000 | >1,000 | >1,000 |
| | 5 | 0.1 | 2.3 | 6.8 | >1,000 | 97 | >1,000 | >1,000 | >1,000 | >500 | 100 |
| Clade C gp140 | 6 | 0.2 | 7.4 | 49.6 | >500 | 132 | >1,000 | >1,000 | >1,000 | >500 | >250 |
| | 7 | 0.1 | 2.4 | 18.9 | >500 | 92 | >500 | >500 | >500 | >500 | >500 |
| | 8 | 0.3 | 6.8 | 29.6 | 134 | 104 | >1,000 | 238 | >250 | >250 | >250 |
| | 9 | 0.4 | 13.4 | 39.1 | >1,000 | 147 | >1,000 | >1,000 | >1,000 | >1,000 | 883 |
| | 10 | 0.2 | 12.6 | 32.4 | >1,000 | 355 | >1,000 | >1,000 | >1,000 | >500 | >1,000 |
| Control | Naïve | >1,000 | >1,000 | >1,000 | >500 | >1,000 | >1,000 | >1,000 | >500 | >1,000 | >1,000 |

Fig. 8

| Trimer | Animal # | Timepoint | Tier 1 Serum NAb Titers (ID50) | | | | | | Control |
| | | | Tier 1 C MW965.26 | Tier 1 A DJ263.8 | Tier 1 B SF162.LS | Tier 1 B BaL.26 | Vaccine 92UG037.8 | Vaccine CZA97.012 | MuLV |
|---|---|---|---|---|---|---|---|---|---|
| Clade C gp140 | 11 | Pre | 49 | 38 | <20 | 27 | 29 | <20 | 34 |
| | | Post-DNA | 31 | 36 | <20 | 66 | 48 | 36 | 43 |
| | | Post-rAd26 | 219 | 119 | <20 | <20 | <20 | <20 | 30 |
| | 12 | Pre | 27 | 25 | <20 | 29 | 29 | <20 | 34 |
| | | Post-DNA | <20 | <20 | <20 | 21 | <20 | <20 | 27 |
| | | Post-rAd26 | 125 | 75 | 25 | 21 | 31 | 23 | 25 |
| | 13 | Pre | 32 | 48 | <20 | <20 | 21 | <20 | 32 |
| | | Post-DNA | 30 | 53 | <20 | 64 | 49 | <20 | 36 |
| | | Post-rAd26 | 67 | 204 | <20 | <20 | 27 | <20 | 38 |
| | 14 | Pre | 48 | 37 | <20 | 32 | 34 | <20 | 43 |
| | | Post-DNA | 42 | 40 | 21 | 107 | 93 | 69 | 71 |
| | | Post-rAd26 | 468 | 322 | 201 | 55 | 76 | 47 | 52 |
| | 15 | Pre | 79 | 38 | <20 | 44 | 46 | <20 | 30 |
| | | Post-DNA | 99 | 120 | 29 | 105 | 154 | 81 | 29 |
| | | Post-rAd26 | 434 | 75 | <20 | <20 | 22 | <20 | 34 |
| Clade A gp140 | 21 | Pre | 31 | 51 | <20 | <20 | 34 | 26 | 63 |
| | | Post-DNA | 54 | 107 | 22 | 83 | 99 | 88 | 136 |
| | | Post-rAd26 | 100 | 381 | 37 | <20 | 27 | <20 | 31 |
| | 22 | Pre | 25 | 31 | <20 | <20 | 23 | 22 | 32 |
| | | Post-DNA | 800 | 186 | 36 | 60 | 76 | 61 | 94 |
| | | Post-rAd26 | 10,275 | 1,118 | 120 | 36 | 36 | <20 | 73 |
| | 23 | Pre | 35 | 40 | <20 | <20 | 42 | 24 | 44 |
| | | Post-DNA | 209 | 78 | 47 | 69 | 83 | 70 | 94 |
| | | Post-rAd26 | 5,231 | 695 | 56 | <20 | 22 | <20 | 31 |
| | 24 | Pre | 46 | 87 | <20 | 51 | 66 | 58 | 73 |
| | | Post-DNA | 1,607 | 75 | 24 | 45 | 71 | 35 | 73 |
| | | Post-rAd26 | 43,822 | 1,053 | 70 | 59 | 54 | 61 | 52 |
| | 25 | Pre | 39 | 50 | <20 | <20 | 55 | 33 | 23 |
| | | Post-DNA | 3,713 | 251 | 25 | 59 | 83 | 58 | 67 |
| | | Post-rAd26 | 11,078 | 693 | <20 | <20 | 27 | <20 | 64 |

Fig. 9

| | | | Tier 1 Serum NAb Titers (ID50) | | | | | | |
|---|---|---|---|---|---|---|---|---|---|
| Trimer | Animal # | Timepoint | Tier 1 C MW965.26 | Tier 1 A DJ263.8 | Tier 1 B SF162.LS | Tier 1 B BaL.26 | Vaccine 92UG037.8 | Vaccine CZA97.012 | Control MuLV |
| Clade C gp140 | 16 | Pre | <20 | 37 | <20 | <20 | 22 | <20 | 40 |
| | | Post-DNA | 459 | 85 | <20 | 31 | 43 | 21 | 37 |
| | | Post-protein | 1,477 | 45 | <20 | <20 | <20 | <20 | <20 |
| | 17 | Pre | 24 | 32 | 26 | <20 | 24 | <20 | 47 |
| | | Post-DNA | 44 | 32 | <20 | 26 | 36 | <20 | 40 |
| | | Post-protein | 343 | 82 | <20 | <20 | <20 | <20 | <20 |
| | 18 | Pre | 31 | 74 | 21 | 45 | 57 | 47 | 61 |
| | | Post-DNA | 92 | 34 | <20 | 40 | 70 | 21 | 48 |
| | | Post-protein | 1,965 | 109 | 66 | <20 | <20 | <20 | <20 |
| | 19 | Pre | 47 | 65 | 31 | 26 | 38 | 22 | 46 |
| | | Post-DNA | 45 | 52 | <20 | <20 | 34 | 20 | 40 |
| | | Post-protein | 1,702 | 168 | <20 | <20 | 20 | <20 | <20 |
| | 20 | Pre | 47 | 107 | <20 | 35 | 56 | 43 | 48 |
| | | Post-DNA | 75 | 58 | <20 | 40 | 63 | 28 | 27 |
| | | Post-protein | 1,334 | 109 | <20 | <20 | 35 | 28 | 23 |
| Clade A gp140 | 26 | Pre | 53 | 48 | 25 | 26 | 50 | 33 | 43 |
| | | Post-DNA | 209 | 68 | <20 | <20 | 25 | 25 | 42 |
| | | Post-protein | 3,571 | 161 | 27 | 21 | <20 | <20 | <20 |
| | 27 | Pre | 36 | 39 | <20 | <20 | 47 | 25 | 36 |
| | | Post-DNA | 250 | 103 | <20 | 33 | 59 | 42 | 66 |
| | | Post-protein | 7,431 | 569 | 120 | <20 | <20 | <20 | <20 |
| | 28 | Pre | 53 | 64 | <20 | 33 | 64 | 43 | 55 |
| | | Post-DNA | 52 | 49 | 51 | 65 | 83 | 72 | 92 |
| | | Post-protein | 588 | 156 | 49 | 42 | 47 | 31 | 53 |
| | 29 | Pre | 78 | 81 | 37 | 38 | 66 | 44 | 47 |
| | | Post-DNA | 219 | 127 | 22 | 47 | 56 | 55 | 70 |
| | | Post-protein | 3,501 | 123 | <20 | <20 | <20 | <20 | <20 |
| | 30 | Pre | 69 | 52 | <20 | <20 | <20 | <20 | 22 |
| | | Post-DNA | 202 | 153 | <20 | 53 | 112 | 62 | 74 |
| | | Post-protein | 15,157 | 531 | 125 | 28 | 20 | <20 | <20 |

Fig. 9 (Cont.)

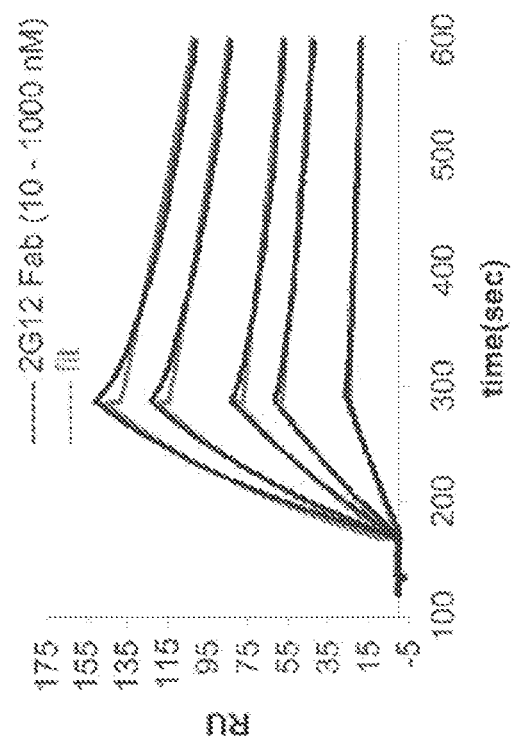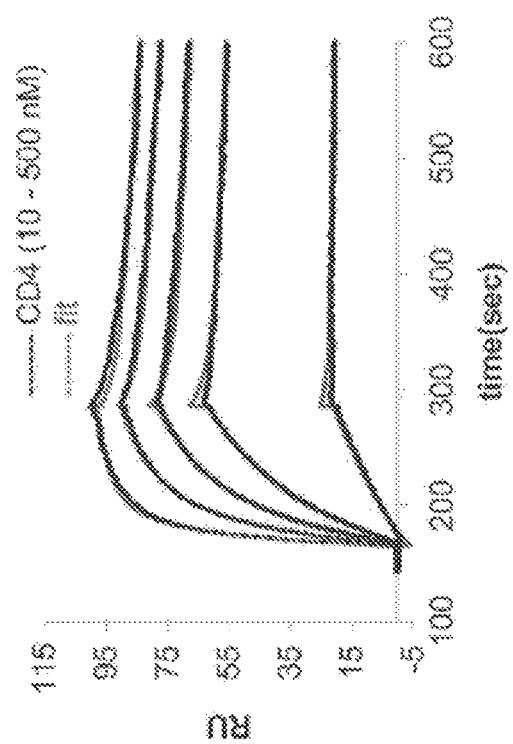
Fig. 10

SEQUENCE LISTING

```
<160> NUMBER OF SEQ ID NOS: 8

<210> SEQ ID NO 1
<211> LENGTH: 723
<212> TYPE: PRT
<213> ORGANISM: Artificial Sequence
<220> FEATURE:
<223> OTHER INFORMATION: Sequence of the 92UG037.8-gp140-6xHis trimer

<400> SEQUENCE: 1

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Thr Val Tyr Gly Val Pro Val Trp Lys Asp Ala Glu
            35                  40                  45

Thr Thr Leu Phe Cys Ala Ser Asp Ala Lys Ala Tyr Asp Thr Glu Val
```

-continued

```
            50                  55                  60
His Asn Val Trp Ala Thr His Ala Cys Val Pro Thr Asp Pro Asn Pro
 65                  70                  75                  80

Gln Glu Ile Tyr Met Glu Asn Val Thr Glu Phe Asn Met Trp Lys
                 85                  90                  95

Asn Asn Met Val Glu Gln Met His Thr Asp Ile Ile Ser Leu Trp Asp
                    100                 105                 110

Gln Ser Leu Lys Pro Cys Val Gln Leu Thr Pro Leu Cys Val Thr Leu
                115                 120                 125

Asp Cys Ser Tyr Asn Ile Thr Asn Asn Ile Thr Asn Ser Ile Thr Asn
            130                 135                 140

Ser Ser Val Asn Met Arg Glu Glu Ile Lys Asn Cys Ser Phe Asn Met
145                 150                 155                 160

Thr Thr Glu Leu Arg Asp Lys Asn Arg Lys Val Tyr Ser Leu Phe Tyr
                    165                 170                 175

Lys Leu Asp Val Val Gln Ile Asn Asn Gly Asn Asn Ser Ser Asn Leu
                180                 185                 190

Tyr Arg Leu Ile Asn Cys Asn Thr Ser Ala Leu Thr Gln Ala Cys Pro
            195                 200                 205

Lys Val Thr Phe Glu Pro Ile Pro Ile Arg Tyr Cys Ala Pro Ala Gly
                210                 215                 220

Tyr Ala Ile Leu Lys Cys Asn Asp Lys Glu Phe Asn Gly Thr Gly Leu
225                 230                 235                 240

Cys Lys Asn Val Ser Thr Val Gln Cys Thr His Gly Ile Arg Pro Val
                    245                 250                 255

Val Ser Thr Gln Leu Leu Leu Asn Gly Ser Leu Ala Glu Gly Lys Val
                260                 265                 270

Met Ile Arg Ser Glu Asn Ile Thr Asn Asn Val Lys Asn Ile Ile Val
            275                 280                 285

Gln Leu Asn Glu Thr Val Thr Ile Asn Cys Thr Arg Pro Asn Asn Asn
    290                 295                 300

Thr Arg Lys Ser Val Arg Ile Gly Pro Gly Gln Thr Phe Tyr Ala Thr
305                 310                 315                 320

Gly Asp Ile Ile Gly Asp Ile Arg Gln Ala His Cys Asn Val Ser Gly
                    325                 330                 335

Ser Gln Trp Asn Arg Ala Leu His Gln Val Val Gly Gln Leu Arg Glu
                340                 345                 350

Tyr Trp Asn Thr Thr Ile Ile Phe Lys Asn Ser Ser Gly Gly Asp Leu
            355                 360                 365

Glu Ile Thr Thr His Ser Phe Asn Cys Gly Gly Glu Phe Phe Tyr Cys
    370                 375                 380

Asn Thr Ser Gly Leu Phe Asn Ser Asn Trp Thr His Asn Asp Thr Ala
385                 390                 395                 400

Ser Met Lys Pro Asn Asp Thr Ile Thr Leu Pro Cys Arg Ile Lys Gln
                    405                 410                 415

Ile Ile Asn Met Trp Gln Arg Val Gly Gln Ala Ile Tyr Ala Pro Pro
                420                 425                 430

Ile Gln Gly Val Ile Arg Cys Glu Ser Asn Ile Thr Gly Leu Ile Leu
            435                 440                 445

Thr Arg Asp Gly Gly Gly Asn Ile Asn Glu Ser Gln Ile Phe Arg Pro
    450                 455                 460

Gly Gly Gly Asp Met Arg Asp Asn Trp Arg Ser Glu Leu Tyr Lys Tyr
465                 470                 475                 480
```

```
Lys Val Val Arg Ile Glu Pro Leu Gly Val Ala Pro Thr Lys Ala Lys
                485                 490                 495

Arg Arg Val Val Glu Arg Glu Lys Arg Ala Val Val Glu Leu Gly Ala
            500                 505                 510

Val Phe Ile Gly Phe Leu Gly Thr Ala Gly Ser Thr Met Gly Ala Ala
        515                 520                 525

Ser Ile Thr Leu Thr Val Gln Val Arg Lys Leu Leu Ser Gly Ile Val
    530                 535                 540

Gln Gln Gln Ser Asn Leu Leu Arg Ala Ile Glu Ala Gln Gln His Leu
545                 550                 555                 560

Leu Lys Leu Thr Val Trp Gly Ile Lys Gln Leu Gln Ala Arg Val Leu
                565                 570                 575

Ala Val Glu Arg Tyr Leu Arg Asp Gln Gln Leu Leu Gly Ile Trp Gly
            580                 585                 590

Cys Ser Gly Lys Leu Ile Cys Thr Thr Asn Val Pro Trp Asn Ser Ser
        595                 600                 605

Trp Ser Asn Lys Ser Glu Arg Glu Ile Trp Glu Asn Met Thr Trp Leu
    610                 615                 620

Gln Trp Asp Lys Glu Ile Ser Asn Tyr Thr His Ile Ile Tyr Glu Leu
625                 630                 635                 640

Ile Glu Glu Ser Gln Lys Gln Gln Glu Lys Asn Glu Gln Leu Leu
                645                 650                 655

Glu Leu Asp Lys Trp Ala Asn Leu Trp Asn Trp Phe Asp Ile Ser Asn
            660                 665                 670

Trp Leu Trp Tyr Ile Lys Glu Phe Ser Arg Ile Glu Gly Arg Gly Ser
        675                 680                 685

Gly Gly Tyr Ile Pro Glu Ala Pro Arg Asp Gly Gln Ala Tyr Val Arg
    690                 695                 700

Lys Asp Gly Glu Trp Val Leu Leu Ser Thr Phe Leu Gly His His His
705                 710                 715                 720

His His His

<210> SEQ ID NO 2
<211> LENGTH: 715
<212> TYPE: PRT
<213> ORGANISM: Artificial Sequence
<220> FEATURE:
<223> OTHER INFORMATION: Sequence of the CZA97.012-gp140-6xHis Trimer

<400> SEQUENCE: 2

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Gly Asn Met Trp Val Thr Val Tyr Tyr Gly Val Pro Val
        35                  40                  45

Trp Thr Asp Ala Lys Thr Thr Leu Phe Cys Ala Ser Asp Thr Lys Ala
    50                  55                  60

Tyr Asp Arg Glu Val His Asn Val Trp Ala Thr His Ala Cys Val Pro
65                  70                  75                  80

Thr Asp Pro Asn Pro Gln Glu Ile Val Leu Glu Asn Val Thr Glu Asn
                85                  90                  95

Phe Asn Met Trp Lys Asn Asp Met Val Asp Gln Met His Glu Asp Ile
            100                 105                 110
```

-continued

```
Ile Ser Leu Trp Asp Gln Ser Leu Lys Pro Cys Val Lys Leu Thr Pro
            115                 120                 125

Leu Cys Val Thr Leu His Cys Thr Asn Ala Thr Phe Lys Asn Asn Val
        130                 135                 140

Thr Asn Asp Met Asn Lys Glu Ile Arg Asn Cys Ser Phe Asn Thr Thr
145                 150                 155                 160

Thr Glu Ile Arg Asp Lys Lys Gln Gln Gly Tyr Ala Leu Phe Tyr Arg
                165                 170                 175

Pro Asp Ile Val Leu Leu Lys Glu Asn Arg Asn Ser Asn Asn Ser
            180                 185                 190

Glu Tyr Ile Leu Ile Asn Cys Asn Ala Ser Thr Ile Thr Gln Ala Cys
        195                 200                 205

Pro Lys Val Asn Phe Asp Pro Ile Pro Ile His Tyr Cys Ala Pro Ala
    210                 215                 220

Gly Tyr Ala Ile Leu Lys Cys Asn Asn Lys Thr Phe Ser Gly Lys Gly
225                 230                 235                 240

Pro Cys Asn Asn Val Ser Thr Val Gln Cys Thr His Gly Ile Lys Pro
                245                 250                 255

Val Val Ser Thr Gln Leu Leu Leu Asn Gly Ser Leu Ala Glu Lys Glu
            260                 265                 270

Ile Ile Ile Arg Ser Glu Asn Leu Thr Asp Asn Val Lys Thr Ile Ile
        275                 280                 285

Val His Leu Asn Lys Ser Val Glu Ile Val Cys Thr Arg Pro Asn Asn
    290                 295                 300

Asn Thr Arg Lys Ser Met Arg Ile Gly Pro Gly Gln Thr Phe Tyr Ala
305                 310                 315                 320

Thr Gly Asp Ile Ile Gly Asp Ile Arg Gln Ala Tyr Cys Asn Ile Ser
                325                 330                 335

Gly Ser Lys Trp Asn Glu Thr Leu Lys Arg Val Lys Glu Lys Leu Gln
            340                 345                 350

Glu Asn Tyr Asn Asn Lys Thr Ile Lys Phe Ala Pro Ser Ser Gly
        355                 360                 365

Gly Asp Leu Glu Ile Thr Thr His Ser Phe Asn Cys Arg Gly Glu Phe
    370                 375                 380

Phe Tyr Cys Asn Thr Thr Arg Leu Phe Asn Asn Asn Ala Thr Glu Asp
385                 390                 395                 400

Glu Thr Ile Thr Leu Pro Cys Arg Ile Lys Gln Ile Ile Asn Met Trp
                405                 410                 415

Gln Gly Val Gly Arg Ala Met Tyr Ala Pro Pro Ile Ala Gly Asn Ile
            420                 425                 430

Thr Cys Lys Ser Asn Ile Thr Gly Leu Leu Leu Val Arg Asp Gly Gly
        435                 440                 445

Glu Asp Asn Lys Thr Glu Glu Ile Phe Arg Pro Gly Gly Gly Asn Met
    450                 455                 460

Lys Asp Asn Trp Arg Ser Glu Leu Tyr Lys Tyr Lys Val Ile Glu Leu
465                 470                 475                 480

Lys Pro Leu Gly Ile Ala Pro Thr Gly Ala Lys Arg Arg Val Val Glu
                485                 490                 495

Arg Glu Lys Arg Ala Val Gly Ile Gly Ala Val Phe Leu Gly Phe Leu
            500                 505                 510

Gly Ala Ala Gly Ser Thr Met Gly Ala Ala Ser Leu Thr Leu Thr Val
        515                 520                 525

Gln Ala Arg Gln Leu Leu Ser Ser Ile Val Gln Gln Gln Ser Asn Leu
```

```
                530                 535                 540
Leu Arg Ala Ile Glu Ala Gln Gln His Met Leu Gln Leu Thr Val Trp
545                 550                 555                 560

Gly Ile Lys Gln Leu Gln Thr Arg Val Leu Ala Ile Glu Arg Tyr Leu
                565                 570                 575

Lys Asp Gln Gln Leu Leu Gly Ile Trp Gly Cys Ser Gly Lys Leu Ile
                580                 585                 590

Cys Thr Thr Asn Val Pro Trp Asn Ser Ser Trp Ser Asn Lys Ser Gln
                595                 600                 605

Thr Asp Ile Trp Asn Asn Met Thr Trp Met Glu Trp Asp Arg Glu Ile
                610                 615                 620

Ser Asn Tyr Thr Asp Thr Ile Tyr Arg Leu Leu Glu Asp Ser Gln Thr
625                 630                 635                 640

Gln Gln Glu Lys Asn Glu Lys Asp Leu Leu Ala Leu Asp Ser Trp Lys
                645                 650                 655

Asn Leu Trp Ser Trp Phe Asp Ile Ser Asn Trp Leu Trp Tyr Ile Lys
                660                 665                 670

Ser Arg Ile Glu Gly Arg Gly Ser Gly Gly Tyr Ile Pro Glu Ala Pro
                675                 680                 685

Arg Asp Gly Gln Ala Tyr Val Arg Lys Asp Gly Glu Trp Val Leu Leu
                690                 695                 700

Ser Thr Phe Leu Gly His His His His His
705                 710                 715

<210> SEQ ID NO 3
<211> LENGTH: 24
<212> TYPE: PRT
<213> ORGANISM: Human immunodeficiency virus type 1

<400> SEQUENCE: 3

Ser Tyr Asn Ile Thr Asn Asn Ile Thr Asn Ser Ile Thr Asn Ser Ser
1               5                   10                  15

Val Asn Met Arg Glu Glu Ile Lys
            20

<210> SEQ ID NO 4
<211> LENGTH: 17
<212> TYPE: PRT
<213> ORGANISM: Human immunodeficiency virus type 1

<400> SEQUENCE: 4

Thr Asn Ala Thr Phe Lys Asn Val Thr Asn Asp Met Asn Lys Glu Ile
1               5                   10                  15

Arg

<210> SEQ ID NO 5
<211> LENGTH: 41
<212> TYPE: PRT
<213> ORGANISM: Human immunodeficiency virus type 1

<400> SEQUENCE: 5

Ser Phe Asn Met Thr Thr Glu Leu Arg Asp Lys Asn Arg Lys Val Tyr
1               5                   10                  15

Ser Leu Phe Tyr Lys Leu Asp Val Val Gln Ile Asn Asn Gly Asn Asn
            20                  25                  30

Ser Ser Asn Leu Tyr Arg Leu Ile Asn
        35                  40
```

```
<210> SEQ ID NO 6
<211> LENGTH: 43
<212> TYPE: PRT
<213> ORGANISM: Human immunodeficiency virus type 1

<400> SEQUENCE: 6

Ser Phe Asn Thr Thr Thr Glu Ile Arg Asp Lys Lys Gln Gln Gly Tyr
1               5                   10                  15

Ala Leu Phe Tyr Arg Pro Asp Ile Val Leu Leu Lys Glu Asn Arg Asn
            20                  25                  30

Asn Ser Asn Asn Ser Glu Tyr Ile Leu Ile Asn
        35                  40

<210> SEQ ID NO 7
<211> LENGTH: 33
<212> TYPE: PRT
<213> ORGANISM: Human immunodeficiency virus type 1

<400> SEQUENCE: 7

Thr Arg Pro Asn Asn Asn Thr Arg Lys Ser Val Arg Ile Gly Pro Gly
1               5                   10                  15

Gln Thr Phe Tyr Ala Thr Gly Asp Ile Ile Gly Asp Ile Arg Gln Ala
            20                  25                  30

His

<210> SEQ ID NO 8
<211> LENGTH: 33
<212> TYPE: PRT
<213> ORGANISM: Human immunodeficiency virus type 1

<400> SEQUENCE: 8

Thr Arg Pro Asn Asn Asn Thr Arg Lys Ser Met Arg Ile Gly Pro Gly
1               5                   10                  15

Gln Thr Phe Tyr Ala Thr Gly Asp Ile Ile Gly Asp Ile Arg Gln Ala
            20                  25                  30

Tyr
```

BIOCHEMICALLY STABILIZED HIV-1 ENV TRIMER VACCINE

CROSS-REFERENCE TO RELATED APPLICATIONS

This application is a continuation of U.S. application Ser. No. 13/082,601, filed on Apr. 8, 2011, which is a continuation of PCT Application No. PCT/US2009/060494 designating the United States and filed Oct. 13, 2009, which was published in the English language on Apr. 15, 2010, under International Publication No. WO2010/042942; which claims the benefit of priority to U.S. Provisional Patent Application No. 61/104,449, filed on Oct. 10, 2008. Each disclosure is incorporated herein by reference in its entirety.

STATEMENT OF GOVERNMENT INTERESTS

This invention was made with Government support under AI084794, AI078526, AI 066924, AI066305 and AI058727 awarded by the National Institutes of Health. The Government has certain rights in the invention.

REFERENCE TO SEQUENCE LISTING SUBMITTED ELECTRONICALLY

This application contains a sequence listing, which is submitted electronically via EFS-Web as an ASCII formatted sequence listing with a file name "689085.3U2 Sequence Listing" and a creation date of Apr. 4, 2017, and having a size of 15 KB. The sequence listing submitted via EFS-Web is part of the specification and is herein incorporated by reference in its entirety.

FIELD

The present invention relates to novel methods and compositions for generating vaccines (e.g., HIV-1 vaccines).

BACKGROUND

Immunogens mimicking the trimeric structure of Envelope (Env) on the native HIV-1 virion are actively being pursued as antibody-based vaccines. However, it has proven difficult to produce biochemically stable, immunogenic, trimeric Env immunogens.

SUMMARY

The present invention is based in part on the discovery of a stabilized trimer of a clade C strain of HIV-1 and the surprising discovery that a stabilized trimer of a clade A strain and a stabilized trimer of a clade C strain were each capable of eliciting a broadly neutralizing antibody response in vivo.

Accordingly, in certain exemplary embodiments, a method of therapeutically treating a subject infected with HIV, e.g., HIV-1, including contacting a subject infected with HIV with an isolated polypeptide comprising a stabilized trimer of an HIV envelope glycoprotein, and producing neutralizing (e.g., broadly neutralizing) antisera in the subject to therapeutically treat the subject is provided. In certain aspects, the method includes neutralizing HIV-1 selected from one or more of clade A, clade B and clade C. In other aspects, the method includes a gp140 trimer. In certain aspects, the gp140 trimer includes one or more variable loop peptides selected from the group consisting of V1, V2 and V3. In other aspects, the gp140 trimer is derived from primary isolate CZA97.012 or 92UG037.8. In certain aspects, HIV titer in the subject infected with HIV is decreased after contacting the subject with the isolated polypeptide.

In certain exemplary embodiments, a method of inhibiting an HIV-mediated activity in a subject in need thereof is provided. The method includes contacting an HIV-infected subject with an isolated polypeptide including a stabilized trimer of an HIV envelope glycoprotein, and producing neutralizing (e.g., broadly neutralizing) antisera in the subject to inhibit the HIV-mediated activity. In certain aspects, the HIV-mediated activity is viral spread. In other aspects, HIV titer in the HIV-infected subject is decreased after contacting the subject with the isolated polypeptide.

In certain exemplary embodiments, a method of preventing HIV infection in a subject is provided. The method includes contacting a subject with an isolated polypeptide comprising a stabilized trimer of an HIV envelope glycoprotein, and inducing in the subject immunity to HIV.

In certain exemplary embodiments, a vaccine is provided. The vaccine includes a stabilized trimer comprising an isolated gp140 polypeptide derived from primary isolate CZA97.012 or primary isolate 92UG037.8 and having an oligomerization domain. The vaccine elicits production of neutralizing (e.g., broadly neutralizing) antisera against HIV after injection into a subject.

In other exemplary embodiments, an isolated, antigenic, stabilized trimer of gp140 is provided. The stabilized trimer includes a gp140 polypeptide derived from primary isolate CZA97.012 or primary isolate 92UG037.8 and an oligomerization domain. The stabilized trimer elicits production of neutralizing (e.g., broadly neutralizing) antisera against HIV after injection into a subject.

In yet other exemplary embodiments, a vector encoding a polynucleotide including an antigenic, stabilized trimer of gp140 is provided. The vector includes a gp140 polypeptide derived from primary isolate CZA97.012 or primary isolate 92UG037.8 and an oligomerization domain. In certain aspects, the stabilized trimer of gp140 includes one or more variable loop peptides selected from the group consisting of V1, V2 and V3. In other aspects, the stabilized trimer of gp140 comprises an amino acid sequence having at least 85%, 90%, 95% or more sequence identity to SEQ ID NO:7 or SEQ ID NO:8. In other aspects, the stabilized trimer of gp140 comprises an amino acid sequence including SEQ ID NO:7 or SEQ ID NO:8. In certain aspects, the stabilized trimer of gp140 elicits production of broadly neutralizing antisera against HIV after injection into a subject.

BRIEF DESCRIPTION OF THE DRAWINGS

(FIG. 2A) pre- and (FIG. 2B) post-immunization. Horizontal line indicates titer>60 cut-off for positivity.

(FIG. 4C) Purified IgG obtained from the sera of representative animals immunized with the clade A (guinea pig #5) and clade C (guinea pig #10) trimers were pre-incubated with linear V3 loop or scrambled peptides and then tested in the TZM.b1 neutralization assays against SF162.LS (tier 1-B), ZM109F.PB4 (tier 2-C) and 6535.3 (Tier 2-B) viruses. (FIG. 4D) Sequence alignment of linear 92UG037.8 (SEQ ID NOs:3, 5 and 7) and CZA97012 (SEQ ID NOs:4, 6 and 8) V1-V3 peptide loops. Amino acid residues highlighted in greyscale indicate homology between sequences at that position.

FIG. 6 depicts HIV-1 tier 1 and 2 neutralization titers of guinea pig sera in TZM-b1 assays. Pre-immunization (Pre) and post $3^{rd}$ trimer vaccination (Post) sera were tested against panels of tier 1 and tier 2 clade A, B and C pseudoviruses in TZM.b1 neutralization assays. Values shown are the serum dilutions representing the ID50 titers for each animal. Values highlighted in yellow indicate positive responses defined as: (i) >3-fold above pre-immune background (ii) >2-fold above a murine leukemia virus (MuLv) control, and (iii) absolute $ID_{50}$ titer>60.

FIG. 7 depicts a summary of NAb titers against tier 2 clade A, B and C viruses. The number and percent of positive samples tested are shown.

FIG. 8 depicts $ID_{50}$ neutralization of select tier 1 and 2 isolates with purified guinea pig IgG. IgG purified from individual guinea pig was tested in TZM.b1 neutralization assays against a select panel of tier 1 and 2 viruses. Data are represented as $IC_{50}$ titers in μg/ml (lower numbers reflect better neutralization). Values highlighted in yellow indicate samples with positive neutralizing activity.

FIG. 9 depicts HIV-1 tier 1 neutralization titers of guinea pig sera in TZM-b1 assays following prime/boost vaccination regimens. Pre-immunization, post-third DNA vaccination, and post rAd26/protein boost sera from guinea pigs were tested for NAb responses against tier 1 viruses in TZM.b1 neutralization assays. Values shown are the serum dilutions representing the ID50 titers for each animal. Highlighted values indicate positive responses.

FIG. 10 depicts a surface plasminogen resonance assay of 92UG037.8-gp140-Fd binding to CD4 (left panel, $K_d$ 1.9 nM), and to 2G12 (right panel, $K_d$=17.9 nM).

FIGS. 12A-12B depicts the amino acid sequences of the 92UG037.8-gp140-6× His trimer (FIG. 12A) (SEQ ID NO:1) and the CZA97.012-gp140-6× His trimer (FIG. 12B) (SEQ ID NO:2).

DETAILED DESCRIPTION

Figure 1A:
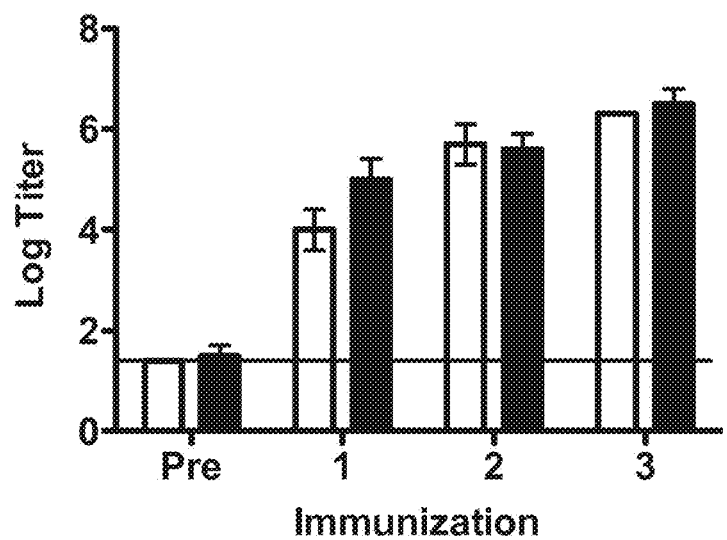
FIGS. 1A-1B graphically depict ELISA titers against gp140 in guinea pig sera. Sera obtained 4 weeks after each immunization were tested in endpoint ELISAs against the clade A and clade C trimers in the (FIG. 1A) clade A and (FIG. 1B) clade C vaccinated guinea pigs. Graphs show geometric mean titers for each time point+/−standard deviation. Horizontal line indicates back ground threshold.

Most antibodies induced by HIV-1 are ineffective at preventing initiation or spread of infection, as they are either non-neutralizing or narrowly isolate-specific. One of the biggest challenges in HIV vaccine development is to design an HIV envelope immunogen that can induce protective, neutralizing antibodies effective against the diverse HIV-1 strains that characterize the global pandemic. Indeed, the generation of "broadly neutralizing" antibodies that recognize relatively conserved regions on the envelope glycoprotein are rare. The present invention is based in part on the discovery of stabilized trimeric HIV-1 envelope proteins that surprisingly elicit a broadly neutralizing antibody response in vivo.

In certain exemplary embodiments, the compounds and methods described herein are used to inhibit or decrease infectivity of one or more pathogens (e.g., viruses, bacteria, fungi, parasites and the like) that have one or more multimeric surface proteins. Accordingly, the present invention is directed in part to stabilized oligomer (e.g., trimer) conformations of the envelope protein (e.g., gp41) of a human immunodeficiency virus (e.g., HIV-1) and methods for their use. In certain aspects, the compounds and methods described herein are used to inhibit or decrease one or more HIV-mediated activities (e.g., infection, fusion (e.g., target cell entry and/or syncytia formation), viral spread and the like) in a subject, which can, in turn, decrease HIV titer.

As used herein, the terms "inhibiting" or "decreasing" with respect to HIV refer to an inhibition or decrease of an HIV-mediated activity (e.g., infection, fusion (e.g., target cell entry and/or syncytia formation), viral spread and the like) and/or a decrease in viral titer. For example, an HIV-mediated activity may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or more.

HIV is a member of the genus Lentivirinae, part of the family of Retroviridae. Two species of HIV infect humans: HIV-1 and HIV-2. As used herein, the terms "human immunodeficiency virus" and "HIV" refer to, but are not limited to, HIV-1 and HIV-2. In certain exemplary embodiments, the envelope proteins described herein refer to those present on any of the five serogroups of lentiviruses that are recognized: primate (e.g., HIV-1, HIV-2, simian immunodeficiency virus (SIV)); sheep and goat (e.g., visna virus, caprine arthritis encephalitis virus); horse (equine infectious anemia virus); cat (e.g., feline immunodeficiency virus (FIV)); and cattle (e.g., bovine immunodeficiency virus (BIV)) (See International Committee on Taxonomy of Viruses descriptions).

HIV is categorized into multiple clades with a high degree of genetic divergence. As used herein, the term "clade" refers to related human immunodeficiency viruses classified according to their degree of genetic similarity. There are currently three groups of HIV-1 isolates: M, N and O. Group M (major strains) consists of at least ten clades, A through J. Group O (outer strains) may consist of a similar number of clades. Group N is a new HIV-1 isolate that has not been categorized in either group M or O. In certain exemplary embodiments, a broadly neutralizing antibody described herein will recognize and raise an immune response against two, three, four, five, six, seven, eight, nine, ten or more clades and/or two or more groups of HIV.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into gp120 and gp140. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

As used herein, the term "oligomer," when used in the context of a protein and/or polypeptide is intended to include, but is not limited to, a protein or polypeptide having at least two subunits. Oligomers include, but are not limited to, dimers, trimers, tetramers, pentamers, hexamers, heptamers, octamers, nonamers, decamers and the like.

As used herein, the term "stabilized oligomer" refers, but is not limited to, an oligomer that includes a protein and/or polypeptide sequence that increases the stability (e.g., via the presence of one or more oligomerization domains) of the oligomeric structure (e.g., reduces the ability of the oligomer to dissociate into monomeric units). In certain exemplary embodiments, a stabilized oligomer is a stabilized trimer.

As used herein, the term "oligomerization domain" refers, but is not limited to, a polypeptide sequence that can be used to increase the stability of an oligomeric envelope protein such as, e.g., to increase the stability of an HIV gp41 trimer. Oligomerization domains can be used to increase the stability of homooligomeric polypeptides as well as heterooligomeric polypeptides. Oligomerization domains are well known in the art.

As used herein, the terms "trimerization domain" and "trimerization tag" refer to an oligomerization domain that stabilizes trimeric polypeptides (e.g., a gp41 homotrimeric polypeptide). Examples of trimerization domain include, but are not limited to, the T4-fibritin "foldon" trimer; the coiled-coil trimer derived from GCN4 (Yang et al. (2002) $J$ $Virol.$ 76:4634); the catalytic subunit of $E.$ $coli$ aspartate transcarbamoylase as a trimer tag (Chen et al. (2004) $J$ $Virol.$ 78:4508). Trimerization domains are well known in the art.

As used herein, the term "protein tag" refers, but is not limited to, a polypeptide sequence that can be added to another polypeptide sequence for a variety of purposes. In certain exemplary embodiments, a protein tag may be removed from a larger polypeptide sequence when it is no longer needed. Protein tags include, but are not limited to, affinity tags (e.g., poly-His tags, chitin binding protein (CBP), maltose binding protein (MBP), glutathione-s-transferase (GST) and the like), solubilization tags (e.g., include thioredoxin (TRX), poly(NANP) MBP, GST and the like), chromatography tags (e.g., polyanionic amino acids such as the FLAG epitope), epitope tags (e.g., FLAG-tag, V5-tag, c-myc-tag, HA-tag and the like), fluorescent tags (e.g., green fluorescent protein (GFP), yellow fluorescent protein (YFP), cyan fluorescence protein (CFP) and the like), bioluminescent tags (e.g., luciferase (e.g., bacterial, firefly, click beetle, sea pansy (Renilla) and the like), luciferin, aequorin and the like), enzyme modification tags (e.g., biotin ligase and the like) and the like. Protein tags are well known in the art and their reagents are often commercially available.

In certain exemplary embodiments, a stabilized trimer of an envelope glycoprotein described herein can be administered to a subject in whom it is desirable to promote an immune response. In other exemplary embodiments, a nucleic acid sequence encoding one or more stabilized trimers of an envelope protein described herein can be administered to a subject in whom it is desirable to promote an immune response.

Accordingly, one or more stabilized oligomers (e.g., stabilized trimers) described herein can be used as immunogens to produce anti-oligomer (e.g., anti-trimer) antibodies in a subject, to inhibit or prevent infection by HIV and/or to inhibit or prevent the spread of HIV in an infected individual. One or more stabilized oligomers (e.g., stabilized trimers) of an envelope glycoprotein described herein can be used as an immunogen to generate antibodies that bind wild-type envelope glycoprotein (i.e., gp41 and/or gp160) using standard techniques for polyclonal and monoclonal antibody preparation.

In certain exemplary embodiments, a stabilized oligomer (e.g., stabilized trimer) of an envelope glycoprotein is capable of eliciting a broadly neutralizing antibody response in a host. As used herein, the terms "neutralizing antibody response" and "broadly neutralizing antibody response" are well known in the art and refer to the ability of one or more antibodies to react with an infectious agent to destroy or greatly reduce the virulence of the infectious agent. The presence of such a response has the potential to prevent the establishment of infection and/or to significantly reduce the number of cells that become infected with HIV, potentially delaying viral spread and allowing for a better control of viral replication in the infected host. A broadly neutralizing antibody against HIV will typically bind a variety of different clades, groups or mutants of HIV.

As used herein, the term "immune response" is intended to include, but is not limited to, T and/or B cell responses, that is, cellular and/or humoral immune responses. The immune response of a subject can be determined by, for example, assaying antibody production, immune cell proliferation, the release of cytokines, the expression of cell surface markers, cytotoxicity, and the like. As used herein, the term "immune cell" is intended to include, but is not limited to, cells that are of hematopoietic origin and play a role in an immune response. Immune cells include, but are not limited to, lymphocytes, such as B cells and T cells; natural killer cells; myeloid cells, such as monocytes, macrophages, eosinophils, mast cells, basophils, and granulocytes.

A stabilized oligomer (e.g., trimer) of an envelope glycoprotein typically is used to prepare antibodies by immunizing a suitable subject, (e.g., rabbit, guinea pig, goat, mouse or other mammal) with the immunogen. An appropriate immunogenic preparation can contain, for example, a recombinantly expressed stabilized trimer of an envelope glycoprotein or a chemically synthesized stabilized trimer of an envelope glycoprotein. The preparation can further include an adjuvant, such as Freund's complete or incomplete adjuvant, Ribi adjuvant, or similar immunostimulatory agent. Immunization of a suitable subject with an immunogenic stabilized oligomer (e.g., trimer) of an envelope glycoprotein preparation induces a polyclonal anti-envelope (e.g., anti-gp41 and/or anti-gp160) antibody response, e.g., an anti-HIV antibody response.

Accordingly, in certain exemplary embodiments, anti-stabilized gp41 trimer antibodies are provided. The term "antibody" as used herein refers to immunoglobulin molecules and immunologically active portions of immunoglobulin molecules, i.e., molecules that contain an antigen binding site which specifically binds (immunoreacts with) an antigen, such as the envelope glycoprotein (e.g., gp41 and/or gp160). Examples of immunologically active portions of immunoglobulin molecules include F(ab) and F(ab')2 fragments which can be generated by treating the antibody with an enzyme such as pepsin. In certain embodiments, polyclonal and/or monoclonal antibodies that bind the envelope glycoprotein (e.g., gp41 and/or gp160) are provided. The term "monoclonal antibody" or "monoclonal antibody composition," as used herein, refers to a population of antibody molecules that contain only one species of an antigen binding site capable of immunoreacting with a particular epitope of the envelope glycoprotein (e.g., gp41 and/or gp160). A monoclonal antibody composition thus typically displays a single binding affinity for a particular the envelope glycoprotein (e.g., gp41 and/or gp160) with which it immunoreacts.

Polyclonal anti-stabilized trimer envelope glycoprotein (e.g., gp41 and/or gp160) antibodies can be prepared as described above by immunizing a suitable subject with a stabilized oligomer (e.g., trimer) of an envelope glycoprotein immunogen as described herein. The anti-stabilized trimer of an envelope glycoprotein antibody titer in the immunized subject can be monitored over time by standard techniques, such as with an enzyme linked immunosorbent assay (ELISA) using immobilized gp41. If desired, the antibody molecules directed against gp41 can be isolated from the mammal (e.g., from the blood) and further purified by well known techniques, such as protein A chromatography to obtain the IgG fraction. At an appropriate time after immunization, e.g., when the anti-gp41 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J Immunol.* 127:539-46; Brown et al. (1980) *J Biol. Chem.* 255:4980-83; Yeh et al. (1976) *Proc. Natl. Acad. Sci. USA* 76:2927-31; and Yeh et al. (1982) *Int. J Cancer* 29:269-75), the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with a stabilized trimer of an envelope glycoprotein immunogen as described above, and the culture supernatants of the resulting hybridoma cells are screened to identify a hybridoma producing a monoclonal antibody that binds gp41.

Any of the many well known protocols used for fusing lymphocytes and immortalized cell lines can be applied for the purpose of generating an anti-stabilized trimer of an envelope glycoprotein monoclonal antibody (see, e.g., G. Galfre et al. (1977) *Nature* 266:55052; Gefter et al. *Somatic Cell Genet.*, cited supra; Lerner, *Yale J. Biol Med.* (supra); Kenneth, *Monoclonal Antibodies*, (supra)). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Particularly suitable immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/0-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of a stabilized trimer of an envelope glycoprotein are detected by screening the hybridoma culture supernatants for antibodies that bind gp41, e.g., using a standard ELISA assay.

Alternative to preparing monoclonal antibody-secreting hybridomas, a monoclonal anti-stabilized trimer of an envelope glycoprotein antibody can be identified and isolated by screening a recombinant combinatorial immunoglobulin library (e.g., an antibody phage display library) with a gp41 protein to thereby isolate immunoglobulin library members that bind gp41. Kits for generating and screening phage display libraries are commercially available (e.g., Recombinant Phage Antibody System, Pfizer, New York, N.Y.; and the SURFZAP™ Phage Display Kit, Stratagene, La Jolla, Calif.). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO92/15679; Breitling et al. PCT International Publication WO93/01288; McCafferty et al. PCT International Publication No. WO 92/01047; Garrard et al. PCT International Publication No. WO 92/09690; Ladner et al. PCT International Publication No. WO90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J* 12:725-734; Hawkins et al. (1992) *J Mol. Biol.* 226:889-896; Clarkson et al. (1991) *Nature* 352:624-628; Gram et al. (1992) *Proc. Natl Acad Sci USA* 89:3576-3580; Garrad et al. (1991) *Bio/Technology* 9:1373-1377; Hoogenboom et al. (1991) *Nucl. Acid Res.* 19:4133-

4137; Barbas et al. (1991) *Proc. Natl. Acad. Sci. USA* 88:7978-7982; and McCafferty et al. (1990) *Nature* 348: 552-554.

Additionally, recombinant anti-stabilized trimer of an envelope glycoprotein antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239: 1534; and Beidler et al. (1988) *J Immunol.* 141:4053-4060.

In certain exemplary embodiments, compositions and methods for enhancing the immune response of a subject to a human immunodeficiency virus are provided. As used herein, the terms "subject" and "host" are intended to include living organisms such as mammals. Examples of subjects and hosts include, but are not limited to, horses, cows, sheep, pigs, goats, dogs, cats, rabbits, guinea pigs, rats, mice, gerbils, non-human primates (e.g., macaques), humans and the like, non-mammals, including, e.g., non-mammalian vertebrates, such as birds (e.g., chickens or ducks) fish or frogs (e.g., *Xenopus*), and non-mammalian invertebrates, as well as transgenic species thereof.

In certain exemplary embodiments, vectors such as, for example, expression vectors, containing a nucleic acid encoding one or more stabilized trimers of an envelope protein described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more stabilized trimers of an envelope protein described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more stabilized trimers of an envelope protein is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., one or more stabilized trimers of an envelope protein).

In certain exemplary embodiments, nucleic acid molecules described herein can be inserted into vectors and used as gene therapy vectors. Gene therapy vectors can be delivered to a subject by, for example, intravenous injection, local administration (see, e.g., U.S. Pat. No. 5,328,470), or by stereotactic injection (see, e.g., Chen et al. (1994) *Proc. Natl. Acad. Sci. USA.* 91:3054). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, adeno-associated virus vectors, and the like, the pharmaceutical preparation can include one or more cells which produce the gene delivery system (See Gardlik et al. (2005) *Med. Sci. Mon.* 11:110; Salmons and Gunsberg (1993) *Hu. Gene Ther.* 4:129; and Wang et al. (2005) *J Virol.* 79:10999 for reviews of gene therapy vectors).

Recombinant expression vectors of the invention can be designed for expression of one or more encoding one or more stabilized trimers of an envelope protein in prokaryotic or eukaryotic cells. For example, one or more vectors encoding one or more stabilized trimers of an envelope protein can be expressed in bacterial cells such as *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40); pMAL (New England Biolabs, Beverly, Mass.); and pRIT5 (Pharmacia, Piscataway, N.J.) which fuse glutathione S-transferase (GST), maltose E binding protein, or protein A, respectively, to the target recombinant protein.

In another embodiment, the expression vector encoding one or more stabilized trimers of an envelope protein is a yeast expression vector. Examples of vectors for expression in yeast *S. cerevisiae* include pYepSec1 (Baldari, et. al., (1987) *EMBO J* 6:229-234); pMFa (Kurjan and Herskowitz, (1982) *Cell* 30:933-943); pJRY88 (Schultz et al., (1987) *Gene* 54:113-123); pYES2 (Invitrogen Corporation, San Diego, Calif.); and picZ (Invitrogen Corporation).

Alternatively, one or more stabilized trimers of an envelope protein can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In certain exemplary embodiments, a nucleic acid described herein is expressed in mammalian cells using a mammalian expression vector. Examples of mammalian expression vectors include pCDM8 (Seed, B. (1987) *Nature* 329:840) and pMT2PC (Kaufman et al. (1987) *EMBO J* 6:187-195). When used in mammalian cells, the expression vector's control functions are often provided by viral regulatory elements. For example, commonly used promoters are derived from polyoma, adenovirus 2, cytomegalovirus and simian virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol* 43:235), in particular promoters of T cell receptors (Winoto and Baltimore (1989) *EMBO J* 8:729) and immunoglobulins (Banetji et al. (1983) *Cell* 33:729; Queen and Baltimore (1983) *Cell* 33:741), neuron-specific promoters (e.g., the neurofilament promoter; Byrne and Ruddle (1989) *Proc. Natl. Acad. Sci. USA.* 86:5473), pancreas-specific promoters (Edlund et al. (1985) *Science* 230:912), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374) and the a-fetoprotein promoter (Campes and Tilghman (1989) *Genes Dev.* 3:537).

In certain exemplary embodiments, host cells into which a recombinant expression vector of the invention has been introduced are provided. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, one or more stabilized trimers of an envelope protein can be expressed in bacterial cells such as *E. coli*, viral cells such as retroviral cells, insect cells, yeast or mammalian cells (such as Chinese hamster ovary cells (CHO) or COS cells). Other suitable host cells are known to those skilled in the art.

Delivery of nucleic acids described herein (e.g., vector DNA) can be by any suitable method in the art. For example, delivery may be by injection, gene gun, by application of the nucleic acid in a gel, oil, or cream, by electroporation, using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI® (Polyplus-transfection Inc., New York, N.Y.), EFFECTENE® (Qiagen, Valencia, Calif.), DREAMFECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

Embodiments of the invention are directed to a first nucleic acid (e.g., a nucleic acid sequence encoding one or more stabilized trimers of an envelope glycoprotein) or polypeptide sequence (e.g., one or more stabilized trimers of an envelope glycoprotein) having a certain sequence identity or percent homology to a second nucleic acid or polypeptide sequence, respectively. Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov (1986) *Nucl. Acids Res.* 14:6745. An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual*, Second Edition, (1989) Cold Spring Harbor, N.Y.; *Nucleic Acid Hybridization: A Practical Approach*, editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization*, supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

A first polynucleotide is "derived from" a second polynucleotide if it has the same or substantially the same base-pair sequence as a region of the second polynucleotide, its cDNA, complements thereof, or if it displays sequence identity as described above. A first polypeptide is derived from a second polypeptide if it is encoded by a first polynucleotide derived from a second polynucleotide, or displays sequence identity to the second polypeptides as described above. In the present invention, when a gp41 protein is "derived from HIV" the gp41 protein need not be explicitly produced by the virus itself, the virus is simply considered to be the original source of the gp41 protein and/or nucleic acid sequences that encode it. Gp41 proteins can, for example, be produced recombinantly or synthetically, by methods known in the art, or alternatively, gp41 proteins may be purified from HIV-infected cell cultures.

In certain exemplary embodiments, one or more antibodies, one or more stabilized trimers of an envelope protein and/or nucleic acid sequences encoding one or more stabilized trimers of an envelope protein described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain exemplary embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating one or more antibodies, one or more stabilized trimers of an envelope protein and/or nucleic acid sequences encoding one or more stabilized trimers of an envelope protein described herein in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, one or more antibodies, one or more stabilized trimers of an envelope protein and/or nucleic acid sequences encoding one or more stabilized trimers of an envelope protein described herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers.

These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

One or more antibodies, one or more stabilized trimers of an envelope protein and/or one or more nucleic acid sequences encoding one or more stabilized trimers of an envelope protein described herein can also be prepared in the form of suppositories (e.g., with conventional suppository bases such as cocoa butter and other glycerides) or retention enemas for rectal delivery.

In one embodiment, one or more antibodies, one or more stabilized trimers of an envelope protein and/or one or more nucleic acid sequences encoding one or more stabilized trimers of an envelope protein described herein are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of one or more antibodies, one or more stabilized trimers of an envelope protein and/or one or more nucleic acid sequences encoding one or more stabilized trimers of an envelope protein described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain exemplary embodiments, a method for treatment of a viral infection, e.g., HIV infection, includes the step of administering a therapeutically effective amount of an agent (e.g., one or more antibodies, one or more stabilized trimers of an envelope protein, a nucleic acid sequence that encodes one or more stabilized trimers of an envelope protein and the like) which modulates (e.g., inhibits), one or more envelope protein (e.g., gp41) activities (e.g., mediating viral fusion (e.g., viral entry and/or syncytia formation)) to a subject. As defined herein, a therapeutically effective amount of agent (i.e., an effective dosage) ranges from about 0.001 to 30 mg/kg body weight, from about 0.01 to 25 mg/kg body weight, from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, in certain exemplary embodiments, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. This example is not to be construed as limiting the scope of the invention as these and other equivalent embodiments will be apparent in view of the present disclosure, figures and accompanying claims.

Example I

Neutralization Capacity of Biochemically Stable HIV-1 gp140 Trimers in a Guinea Pig Model Preclinical evaluation of candidate Env immunogens is critical for concept testing and for prioritization of vaccine candidates. Luciferase-based virus neutralization assays in TZM.b1 cells (Li et al. (2005) *J Virol.* 79:10108; Montefiori (2005) *Curr. Prot. Immunol.* Chapter 12:Unit 1211) have been developed as high throughput assay that can be standardized (Montefiori (2009) *Methods Mol. Biol.* 485:395; Polonis et al. (2008) *Virology* 375:315). However, optimal use of this assay required the generation of standardized virus panels derived from multiple clades and reflecting both easy-to-neutralize (tier 1) and primary isolates (tier 2) viruses (Li et al., Supra).

By screening a panel of primary HIV-1 isolates, two viruses, CZA97.012 (Clade C) (Rodenburg et al. (2001) *AIDS Res. Hum. Retroviruses* 17:161) and 92UG037.8 (Clade A) (Chen et al., Supra) were identified that yielded biochemically homogenous and stable trimers with well-defined and uniform antigenic properties (Burke et al. (2009) *Virology* 387:147). The addition of the T4 bacteriophage fibritin "fold-on" (Fd) trimerization domain further increased their yield and purity (Frey et al. (2008) *Proc. Natl. Acad. Sci. USA* 105:3739). As described further herein, the immunogenicity of these stabilized clade A and clade C gp140 trimers was assessed in guinea pigs using a panel of tier 1 and tier 2 isolates from clades A, B and C.

Production of Stable, Homogenous HIV-1 gp140 Trimers

Figure 13:
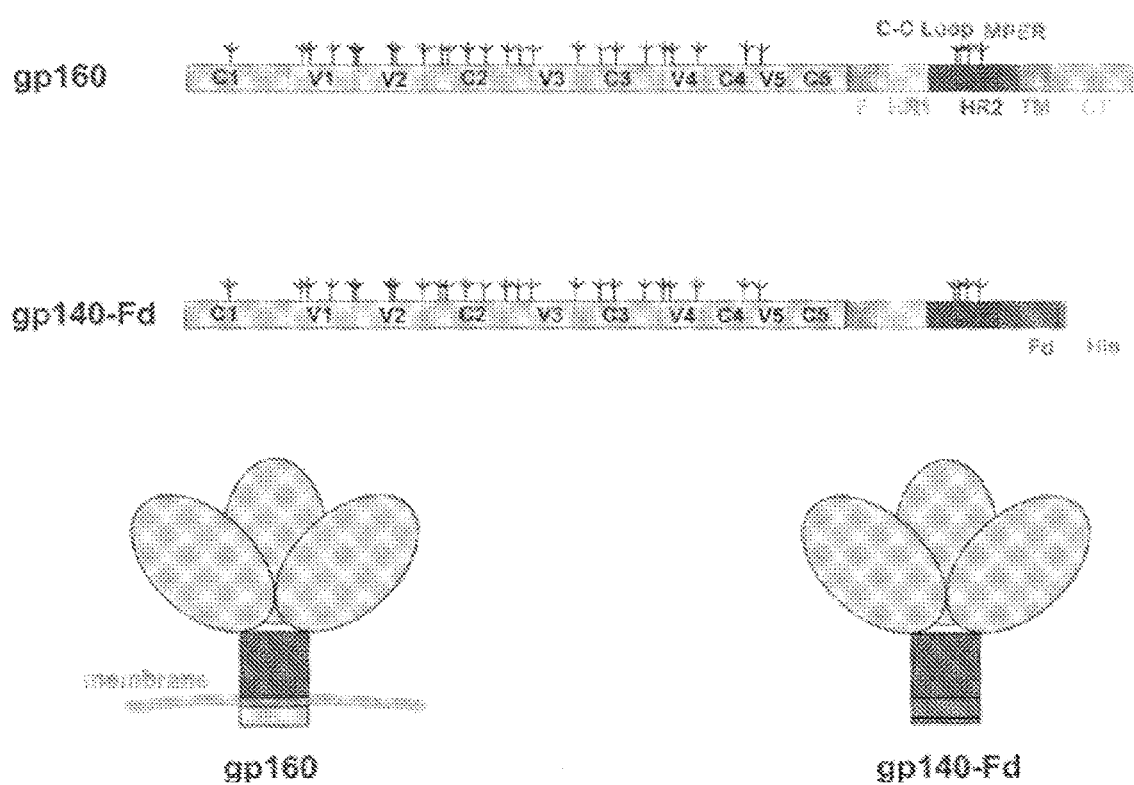
FIG. 13 schematically depicts foldon-stabilized HIV-1 gp140 trimers (gp140-Fd). Gp160 is the full-length precursor. Various segments of gp120 and gp41 are designated as follows: C1-C5, conserved regions 1-5; V1-V5, variable regions 1-5; F, fusion peptide; HR1, heptad repeat 1; C-C loop, the immunodominant loop with a conserved disulfide bond; HR2, heptad repeat 2; MPER, membrane proximal external region; TM, transmembrane anchor; CT, cytoplasmic tail. Gp140-Fd represents the uncleaved ectodomain of gp160 with a T4 fibritin foldon trimerization tag and His tag at its C-terminus.

Env gp140 trimers derived from primary isolates 92UG037.8 (clade A) and CZA97.012 (clade C) were stabilized with a T4-fibritin "foldon" C-terminal trimerization tag (FIG. 13) and produced in *T.ni* (High 5) cells. The biochemical purity and stability was determined as follows: Purified CZA97.012 (clade C) gp140 trimer was resolved by gel-filtration chromatography on Superpose 6 columns. The apparent molecular mass was calculated by using standards thryoglobulin (670 kDa), ferritin (440 kDa), and catalase (232 kDa). Peak fractions were pooled and analyzed by SDS-PAGE. The clade C trimer was treated with various concentrations (0, 0.05, 0.25, 0.5, 1, 2, 5 mM) of ethylene glycol bis(succinimidylsuccinate). Cross-linked products were analyzed by SDS-PAGE using a 4% gel. The molecular standard was cross-linked phosphorylase b (Sigma). Similar analyses have been previously reported for the purified clade A 92UG037.8 gp140 trimer (Frey et al., Supra). The CZA97.012 (clade C) trimer showed similar purity and homogeneity as determined by size exclusion chromatography and chemical cross linking that confirmed that it was monodisperse and trimeric.

A luciferase reporter gene assay was performed in TZM-b1 cells (a genetically engineered cell line that expresses CD4, CXCR4 and CCR5 and contains Tat-inducible Luc and Gal reporter genes) based on single round infection with molecularly cloned Env-pseudotyped viruses. This assay resulted in a high success rate in single round infections, increased assay capacity (e.g., a two day assay), increased precision (e.g., accurately measured 50% neutralization), and an improved level of standardization (e.g., a stable cell line). The luciferase reporter gene assay was optimized and validated.

Binding Antibody Responses Elicited by Clade A and Clade C Trimers

A multi-tiered approach was used to assess vaccine-elicited neutralizing antibody responses. In Tier 1, vaccine strain(s) and neutralization-sensitive strains were not included in the vaccine. In Tier 2, a panel of heterologous viruses matching the genetic subtype(s) of the vaccine (e.g., 12 viruses per panel) was used. This tier could optionally include additional strains from vaccine trial sites. In Tier 3, a multi-clade panel comprised of six Tier 2 viruses evaluated in Tier 2 was used. Tier 3 could optionally include additional strains from an optional vaccine trial site.

In a preliminary study, the immunogenicity of a 92UG037.8 (clade A) gp120 monomer core immunogen was assessed in guinea pigs, which elicited only minimal neutralizing antibody (Nab) responses against tier 1 neutralization sensitive viruses. The immunogenicity of 92UG037.8 (clade A) and CZA97.012 (clade C) trimers that were selected and engineered for maximum stability and conformational homogeneity were then focused on. These immunogens contained the gp140 sequence fused to the T4 fibritin fold-on trimerization domain.

Preliminary 92UG037.8 gp120 monomer experiments were performed as follows. A monomeric 92UG037.8-gp120 'core' that was devoid of V1-V3 regions and had amino- and carboxy-terminal truncations was generated. Guinea pigs were immunized at four week intervals with 100 μg 92UG037.8 gp120 monomer in Ribi adjuvant. Sera were obtained four weeks after each immunization, and were tested against the 92UG037.8 gp120 antigen in an end-point ELISA assay.

Env gp140 trimers derived from primary isolates 92UG037.8 (clade A) and CZA97.012 (clade C) were stabilized with a T4-fibritin foldon C-terminal trimerization tag and produced in *T.ni* cells (HIGH FIVE™, Invitrogen, Carlsbad, Calif.). Initial biochemical analyses were performed by size-exclusion chromatography and chemical cross-linking. 92UG037.8 (clade A) and CZA97.012 (clade C) gp140-Fd trimers were purified to homogeneity and exhibited single peaks as determined by size-exclusion chromatography. Expected molecular weights and oligomerization states were observed for both 92UG037.8 and CZA97.012 trimers by Coomassie staining and chemical cross-linking, respectively. The sedimentation equilibrium of 92UG037.8-gp140-Fd and its in vitro cleavage by human plasmin were determined. The molecular mass was determined to be 409+/−10 kDa (confirming the expected value of approximately 405 kDa).

92UG037.8-gp140-Fd was able to bind both soluble CD4 and monoclonal antibody (mAb) 2G12 (a broadly neutralizing mAb that recognizes carbohydrates on the outer gp120 surface). 92UG037.8-gp140-Fd also bound CD4i mAb 17b (a monoclonal CD4-induced (CD4i) neutralizing antibody that has a binding epitope which partially overlaps with the co-receptor CCR5 binding site of gp120) and cluster I mAbs (mAbs that are non-neutralizing and react with the immunodominant region of gp41 (amino acids 579-613); Cluster II mAbs react with MPER gp41 amino acids 644-667 and are either non-neutralizing or neutralizing (e.g., mAbs 2F5, 4E10, Z13)).

Figure 1B:
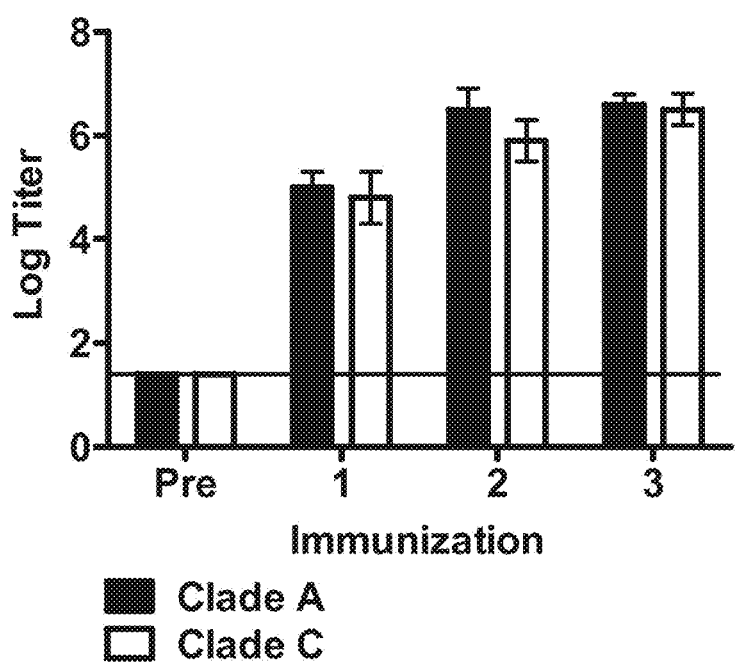

Guinea pigs (n=5/group) were immunized with 100 μg of the clade A or clade C gp140 trimer in Ribi adjuvant s.q./i.p. at weeks 0, 5 and 10. Serum was obtained 4 weeks after each immunization. Env-specific binding antibodies were assessed by endpoint ELISAs to both clade A and clade C gp140. High titer binding antibody responses were observed in both clade A and clade C trimer immunized guinea pigs. Responses were detected after a single immunization and increased to a mean 6.5 log titer following the second and third immunizations (FIGS. 1A-1B). ELISA responses were comparable to the homologous and heterologous gp140 strains (FIGS. 1A-1B).

Neutralizing Antibody Responses Elicited by Clade A and Clade C Trimers

To assess the neutralization profile afforded by the stable clade A and clade C trimers, TZM.b1 assays (Li et al., Supra; Montefiori et al., Supra) were performed using a panel of tier 1 and tier 2 viruses with a broad range of neutralization sensitivities from clades A, B and C. The criteria for was defined as: (i) >3-fold above pre-immune background, (ii) >2-fold above a concurrent murine leukemia virus (MuLv) control, and (iii) an absolute $ID_{50}$ titer>60. Guinea pigs immunized with either clade A or clade C trimers developed robust, cross-clade neutralizing activity against neutralization sensitive tier 1 clade A, B and C viruses (DJ263.8, SF162.LS and MW965.26 respectively) with $ID_{50}$ titers against MW965.26 ranging from 14,274 to 33,847 (FIG. 6). No neutralization was observed against the autologous vaccine strains. Without intending to be bound by scientific theory, this result presumably reflected their inherent neutralization resistant phenotypes.

Figure 2A:
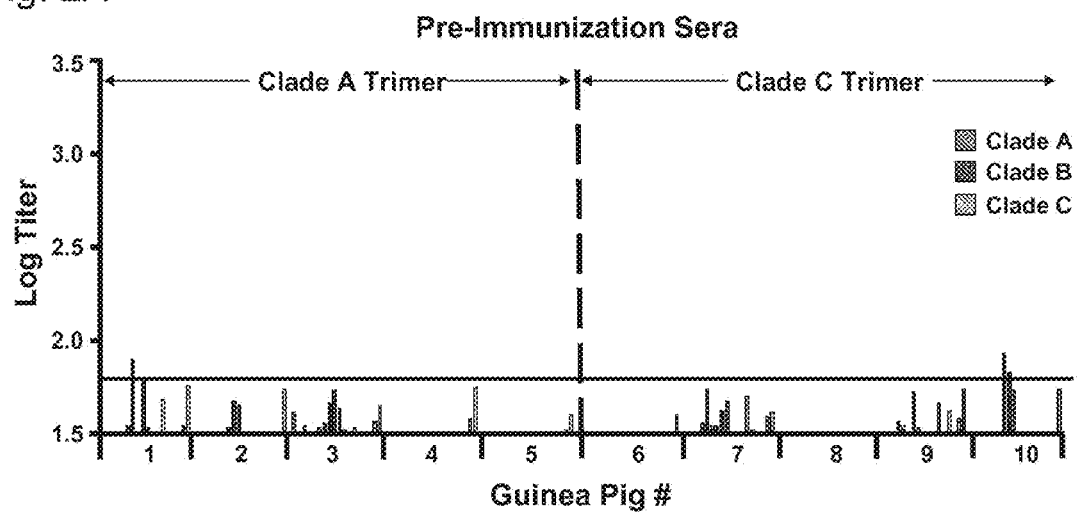
FIGS. 2A-2B graphically depict summaries of neutralizing antibody (NAb) titers against tier 2 viruses. NAb titers against six clade A (red), clade B (blue), and clade C (green) tier 2 primary isolates are summarized for each guinea pig.
Figure 2B:
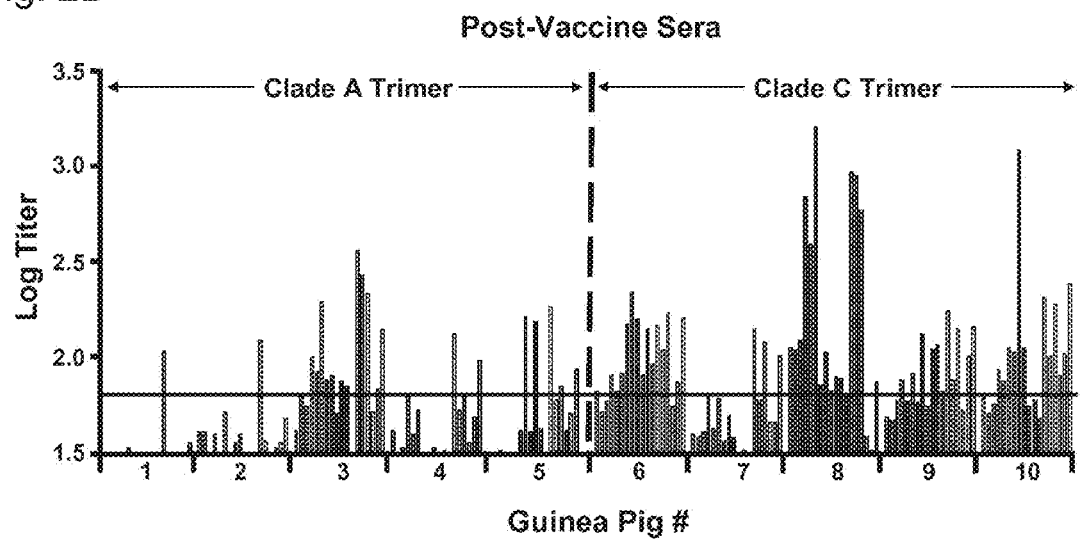

NAb responses were assessed against more stringent tier 2 primary isolate viruses. Lower titer but reproducible neutralization activity against select tier 2 clade A, B and C viruses was detected in sera from animals following immunization (FIG. 6). The magnitude and consistency of responses against tier 2 viruses were substantially lower than against tier 1 viruses. Nevertheless, a degree of tier 2 neutralization activity was consistently observed. Furthermore, the clade C trimer elicited responses of increased magnitude and breadth compared with the clade A trimer. A graphical summary of NAb titers against tier 2 viruses in pre- and post-immunization sera is shown in FIG. 2. Overall, the clade C trimer elicited detectable NAb responses against 27%, 20% and 47% of tier 2 viruses tested from clades A, B and C, respectively, whereas the clade A trimer elicited detectable NAb responses against 13%, 7% and 27% of tier 2 viruses tested from clades A, B and C, respectively (FIG. 7). These data demonstrate the immunogenicity of these stable clade A and clade C trimers and show the utility of this panel of viruses for providing a systematic tiered approach for assessing NAb responses elicited by HIV-I Env immunogens.

Neutralizing Antibody Responses of Purified IgG

Figure 3A:
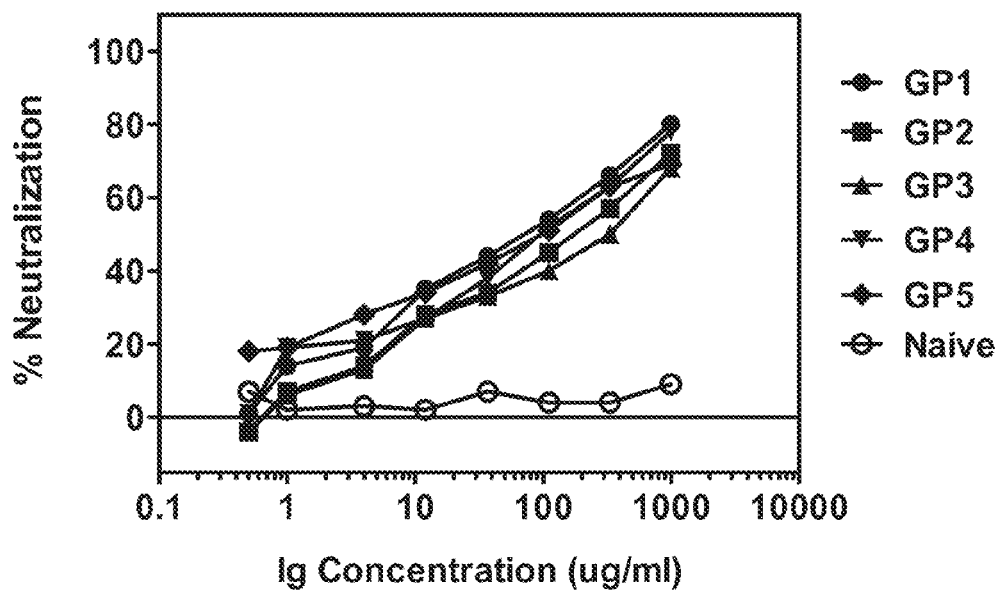
FIGS. 3A-3B graphically depict sample raw neutralization data with purified IgG against the tier 2 clade C virus ZM109F.PB4. Serial dilutions of purified IgG from (FIG. 3A) clade A or (FIG. 3B) clade C trimer immunized guinea pigs and naive control animals were tested for NAb activity against the tier 2 clade C virus ZM109F.PB4.
Figure 3B:
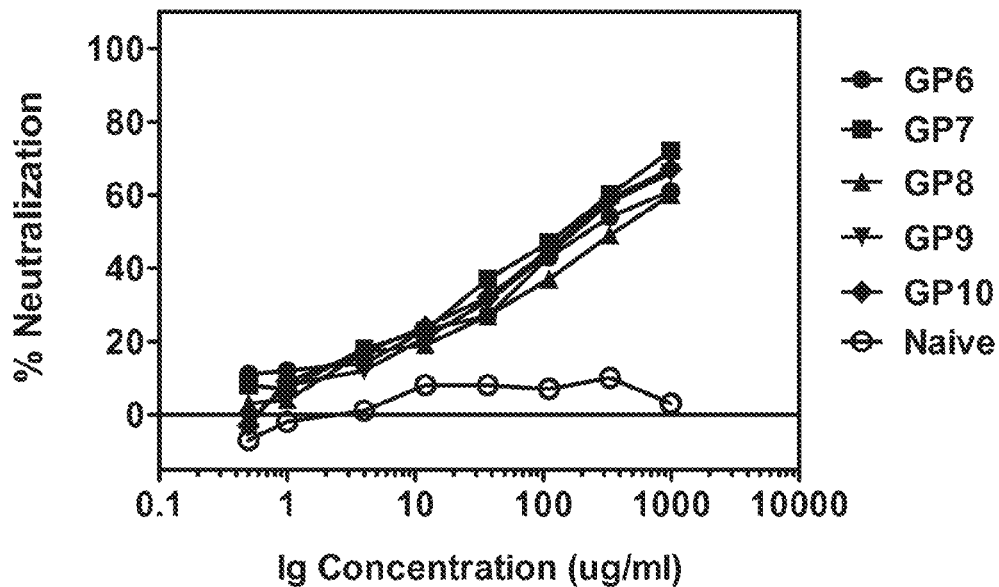

To confirm the results of the NAb assays using serum, additional neutralization assays were performed using IgG purified from serum of immunized animals. Purified IgG demonstrated potent neutralizing activity against the panel of tier I viruses at low concentrations (0.1-0.4 μg/ml for MW965.26) as well as detectable neutralization activity against a limited number of tier 2 viruses including ZMI97M.PB7, ZMIO9F.PB4, 0439.v5.ci and 6535.3 (FIG. 8). Sample raw virus neutralization data using purified IgG against the clade C tier 2 virus ZMIO9F.PB4 is shown in FIG. 3. Control IgG from naive sera exhibited no neutralization activity.

Variable Loop Peptide Responses

Figure 4A:
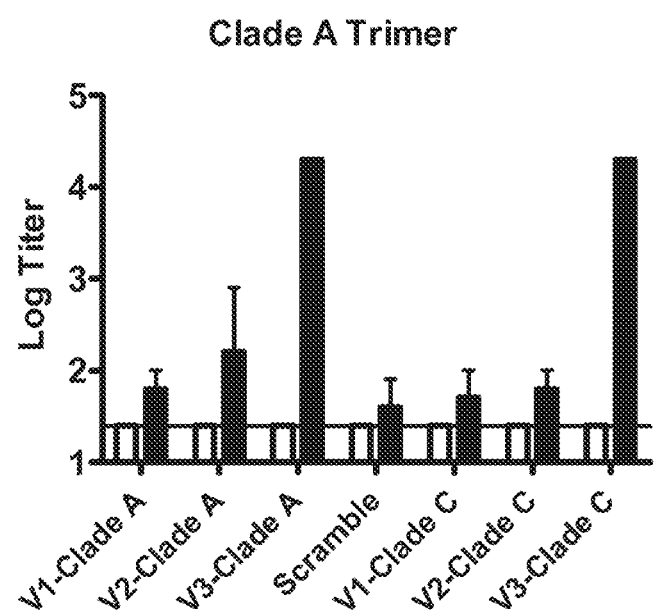
FIGS. 4A-4D depict antibody responses to variable loop peptides. Pre- and post-immunization sera from (FIG. 4A) clade A and (FIG. 4B) clade C trimer immunized animals were assessed by ELISA against homologous and heterologous V1, V2 and V3 loop peptides. Graph depicts geometric mean titers for each group+/−standard deviation. Horizontal line indicates background threshold.
Figure 4B:
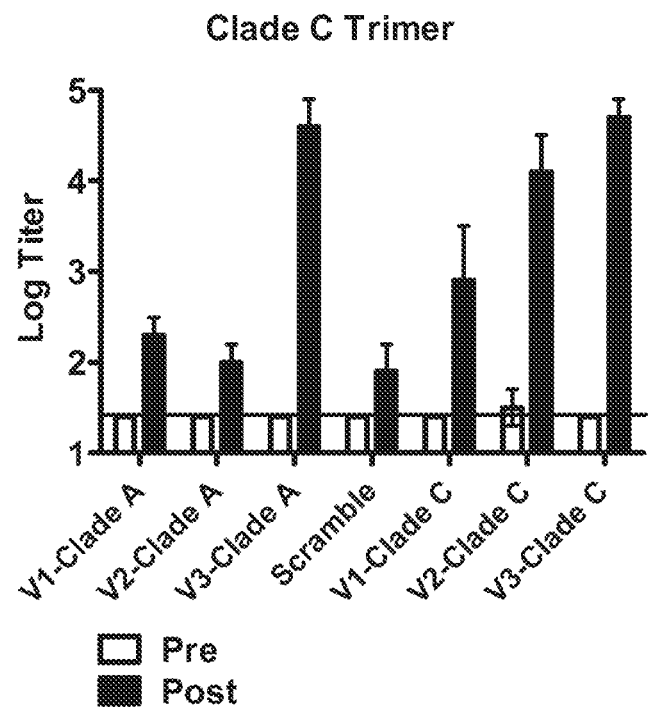
Figures 4C, 4D:
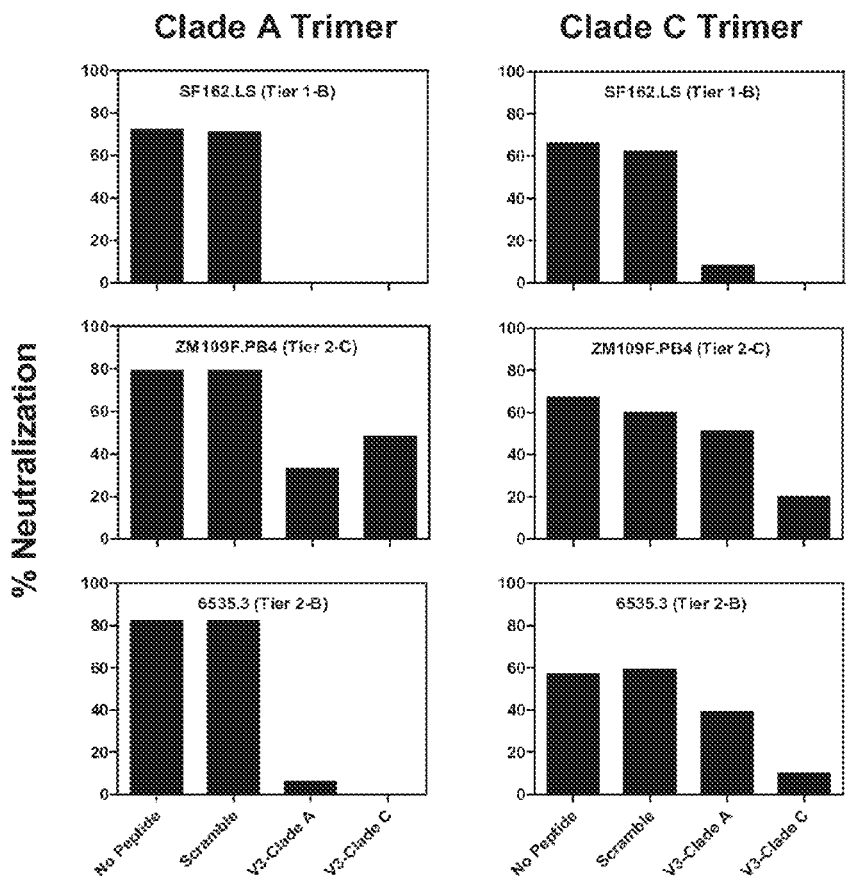

Antibody responses against V1, V2 and V3 peptides from clade A 92UG037.8 and clade C CZA97.012 gp140 were assessed. A scrambled 92UG037.8 V3 peptide was utilized as a negative control. Sera from guinea pigs immunized with both clade A and clade C trimers exhibited ELISA responses against linear V3 loop peptides but not against the scrambled peptide (FIGS. 4A-4B). These responses were comparable against homologous and heterologous V3 sequences, and lower ELISA titers were observed against V1 and V2 peptides. V3 peptide competition neutralization assays were performed from representative animals that received the clade A (guinea pig #5) and clade C (guinea pig #10) trimers. Neutralizing activity against select tier 1 and tier 2 viruses was partially blocked by both homologous and heterologous V3 loop peptides but not by the scrambled peptide (FIG. 4C), indicating that the clade A and clade C gp140 trimers elicited NAbs that were directed in part against conserved elements in the V3 loop. Sequence alignment of the V3 loops of 92UG037.8 and CZA97.012 showed substantial sequence homology (FIG. 4D).

Heterologous Prime/Boost Regimens

Figure 5A:
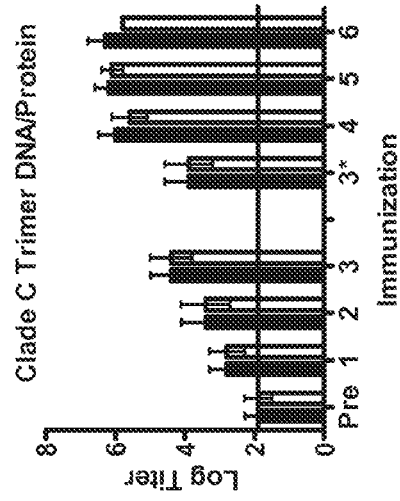
FIGS. 5A-5D graphically depict ELISA titers against gp140 following heterologous prime/boost vaccination regimens. Sera obtained 4 weeks after each immunization in the DNA/protein boost groups (FIG. 5A, FIG. 5B) and the DNA/rAd26 groups (FIG. 5C, FIG. 5D) groups were assessed by ELISAs. Graphs show geometric mean titers for each time point+/−standard deviation. 3* indicates ELISA titers after 3 immunizations but prior to boosting. Horizontal line indicates background threshold.
Figure 5B:
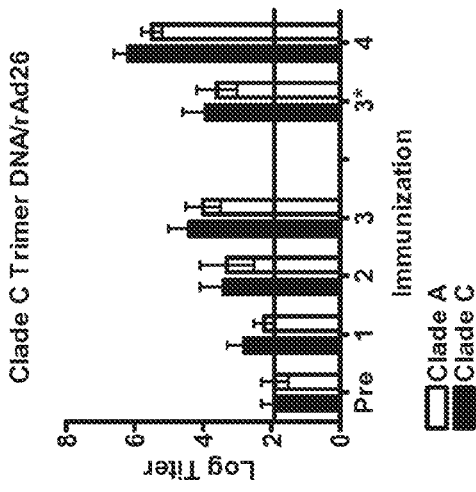
Figure 5C:
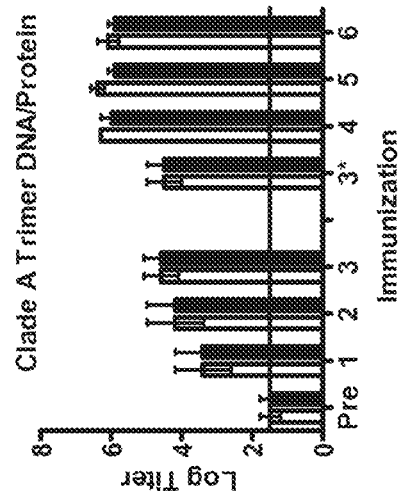
Figure 5D:
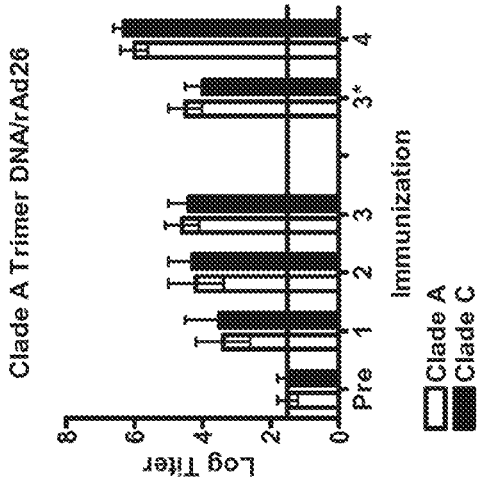
Figure 11:
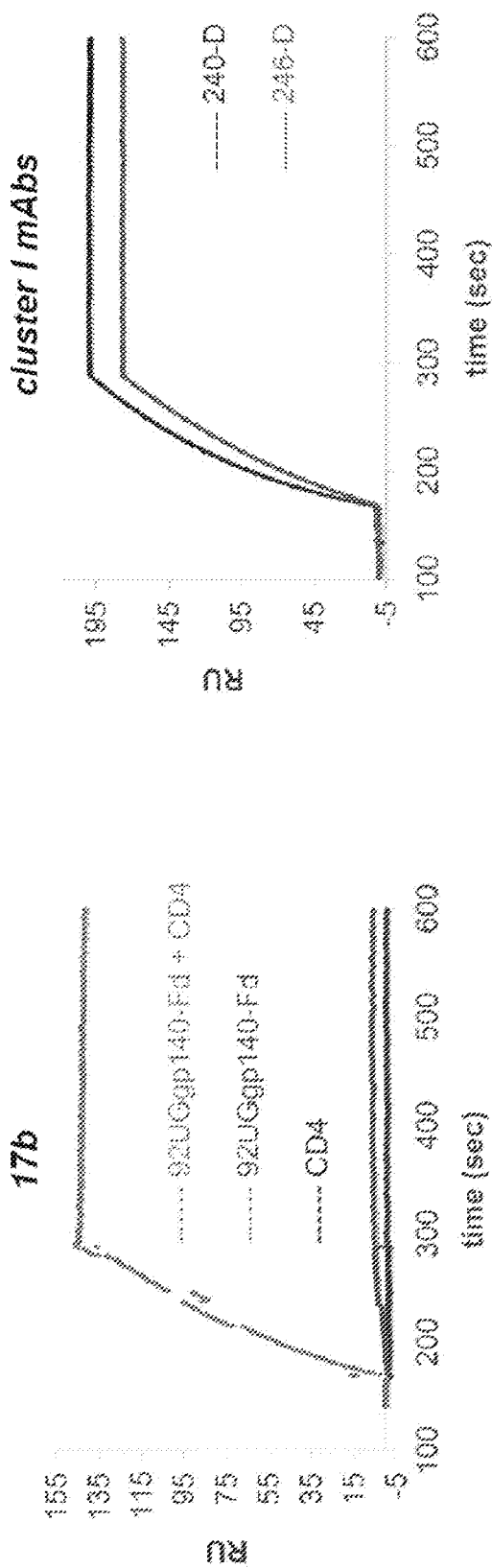
FIG. 11 depicts a surface plasminogen resonance assay of 92UG037.8-gp140-Fd binding to mAb 17b (left panel), and to Cluster I mAbs (right panel).

DNA priming followed by protein boosting has previously been reported to elicit higher titer antibody responses than either approach alone (Vaine et al. (2008) *J Virol.* 82:7369; Wang et al. (2006) *Virology* 350:34). Accordingly, DNA prime, protein boost as well as DNA prime, recombinant adenovirus serotype 26 (rAd26) boost regimens expressing the clade A and clade C trimers were explored. Guinea pigs (n=5/group) were primed with 0.5 mg DNA vaccines intramuscularly (i.m.) at weeks 0, 4, and 8 and then boosted at week 36 with a single immunization of rAd26 vectors or at weeks 36, 40, and 44 with trimer proteins in Ribi adjuvant. High titer, ELISA responses were observed following immunization with both the DNA/protein (FIGS. 5A-5B) and the DNA/rAd26 (FIGS. 5C-5D) regimens. Peak titers obtained after the three DNA priming immunizations were a mean log titer of 4.8. Boosting with either a single rAd26 or three purified protein immunizations augmented responses to mean log titers of 6.5, which were comparable to those elicited by the protein only regimen (FIG. 1).

Low levels of tier 1 NAb responses were observed after DNA priming (FIG. 9). However, following boosting, the DNA/rAd26 and the DNA/protein regimens did not induce higher titer tier 1 NAb responses as compared with the protein-only regimen. Without intending to be bound by scientific theory, it is though that the DNA vaccines may have elicited a variety of gp140 protein conformers or oligomers that could have primed non-neutralizing antibody responses. These data suggest that, in certain settings, prime/ boost vaccine regimens may not necessarily prove superior to purified protein immunogens.

Discussion

The data presented herein assessed the immunogenicity of highly purified CZA97.012 (clade C) and 92UG037.8 (clade A) Env gp140 trimer immunogens that were selected and engineered for optimal biochemical stability and conformational homogeneity. Most Env trimer immunogens reported to date are derived from clade B isolates, although recent reports have also described trimers from other clades (Burke et al., Supra; Kang et al. (2009) Vaccine 37:5120, Epub 2009 Jun. 28). However, the conformational homogeneity of those preparations was often not fully assessed. A panel of tier 1 and tier 2 from clades A, B and C viruses with a broad range of neutralization sensitivities were utilized to assess virus neutralization. Guinea pigs immunized with clade A and clade C trimers demonstrated robust, cross-clade neutralizing activity against neutralization sensitive tier 1 clade A, B and C viruses, as well as clear but low levels of neutralizing activity against select tier 2 clade A, B and C viruses. NAb responses against tier 2 isolates were confirmed using purified IgG but were substantially lower in magnitude and less consistent than responses against tier 1 isolates. Antibody responses elicited by the trimers were directed in part against the V1, V2 and V3 loops. V3 loop reactivity was observed against both heterologous viruses, although, without intending to be bound by scientific theory, it is likely that a variety of other epitopes were also targeted.

Heterologous prime/boost vaccination regimens were also assessed for their potential to augment the immunogenicity of the trimer protein immunogens. DNA/protein and DNA/rAd26 regimens did not lead to improved magnitude or breadth of antibody responses as compared with the protein-only regimen. In fact, the prime/boost regimens appeared to elicit lower NAb responses despite comparable ELISA binding antibody responses. These finding contrast with previous reports highlighting the improved humoral responses obtained with DNA/protein or DNA/rAd regimens as compared to protein-only regimens in other systems (Seaman et al. (2005) J. Virol. 79:2956; Vaine et al., Supra; Wang et al. (2005) J. Virol. 79:7933; Wang et al., Supra). It is hypothesized that the lower NAb activity observed in prime/boost regimens in the present study may have been related to a heterogeneous mixture of Env conformers or oligomers expressed by DNA vaccines, which could have skewed the antibody responses towards non-neutralizing epitopes. Taken together, these findings indicate that the optimal regimen may be dependant on the particular antigen or system utilized.

In summary, the results described herein demonstrate the immunogenicity of clade A and clade C trimers that have been selected and engineered for optimal purity and stability. Importantly, the panel of tier 1 and tier 2 viruses from clades A, B, and C allows a rapid assessment of NAb profiles against a diversity of viruses and may prove useful for comparative immunogenicity studies of novel candidate HIV-1 Env immunogens.

Example II

Materials and Methods

HIV-1 gp140 Trimers

92UG037.8 (clade A) and CZA97.012 (clade C) gp140 trimers with a C-terminal T4 bacteriophage fibritin trimerization domain (foldon) and poly-histidine motif were expressed in insect cells using the Bac-to-Bac system (Invitrogen) as previously described (Chen et al. (2000) J Biol. Chem. 275:34946; Frey et al., Supra). Briefly, recombinant baculovirus was generated according to the manufacturer's protocol and amplified in Sf9 insect cells. For large-scale production, 12 liters of Trichoplusia ni (Hi-5) cells ($2 \times 10^6$ cells/ml) were infected at the optimal multiplicity of infection. The supernatant was harvested 68 hours post infection by centrifugation and concentrated to 2 liters, followed by immediately exchanging into phosphate buffered saline (PBS) in a tangential flow filtration system, ProFlux M 12 (Millipore). After a clarifying spin and adding imidazole to the final concentration of 15 mM, the supernatant was loaded onto a nickel column at a flow rate of 1 ml/min, then washed with 15 mM imidazole in PBS, followed by further sequential washes with 40 mM and 60 mM imidazole in PBS. The protein was eluted with 300 mM imidazole in PBS. The fractions containing the purified protein were pooled, concentrated, and further purified by gel filtration chromatography on Superose 6 (GE Healthcare). The protein was concentrated, frozen in liquid nitrogen, and stored at $-80°$ C.

DNA Vaccines

Human codon optimized gene sequences for the clade C and clade A gp140 trimers with a C-terminal T4 bacteriophage fibritin trimerization domain (Bower et al. (2004) J. Virol. 78:4710; Yang et al. (2002) J. Virol. 76:4634) and poly-histidine motif were synthesized commercially (Geneart) and cloned into the SaII-BamHI restriction sites of a pCMV eukaryotic expression vector. Gene inserts were verified by diagnostic restriction digests, DNA sequencing and expression testing in 293 cells. Endo-toxin free preparations of pCMV-CZA97012-gp140 and pCMV-92UG037-gp140 (Qiagen) were utilized for immunization protocols.

Recombinant Adenovirus Serotype 26 Vectors

Replication-incompetent, E1/E3-deleted recombinant adenovirus serotype 26 (rAd26) vectors expressing clade A and clade C gp140 trimers with a C-terminal T4 bacteriophage fibritin trimerization foldon domain (Bower et al., Supra; Yang et al., Supra) and poly-histidine motif were prepared as previously described (Abbink et al. (2007) J. Virol. 81:4654).

Animals and Immunizations

Outbred female Hartley guinea pigs (Elm Hill) were housed at the Animal Research Facility of Beth Israel Deaconess Medical Center under approved Institutional Animal Care and Use Committee (IACUC) protocols. Protein trimer, (100 μg/animal) were administered at 4 or 5 week intervals in 500 μl PBS in Ribi adjuvant (Sigma) at three sites: 2 subcutaneous (sq) (200 μl/site) and 1 intraperitoneal (i.p.) (100 μl/site). Endo-toxin free DNA vaccines (500 μg/animal) were administered intramuscularly in 500 μl PBS divided between the right and left quadriceps at 4-week intervals. Recombinant Ad26 vectors ($5 \times 10^{10}$ vp/animal) were administered intramuscularly in 500 μl saline divided between the right and left quadriceps. Serum samples were obtained in anesthetized animals from the vena cava.

ELISA

Serum binding antibody titers against gp140 trimers and linear peptides (New England Peptide) were determined by an end point ELISAs. Ninety-six well maxisorp ELISA plates (Thermo Fisher Scientific) coated overnight with 100 μl/well of 1 μg/ml clade A gp140, Clade C gp140 or V1-V3 linear peptide loops in PBS were blocked for 3 hours with PBS containing 2% BSA (Sigma) and 0.05% Tween 20 (Sigma). Guinea pig sera were then added in serial dilutions and incubated for 1 hour at room temperature. The plates were washed three times with PBS containing 0.05% Tween 20 and incubated for 1 hour with a 1/2000 dilution of a HRP-conjugated goat anti-guinea pig secondary antibody (Jackson ImmunoResearch Laboratories). The plates were washed three times and developed with SureBlue TMB microwell peroxidase (KPL Research Products), stopped by addition of TMB stop solution (KPL Research products) and analyzed at dual wavelengths 450 nm/550 nm on a Spectramax Plus ELISA plate reader (Molecular Devices) using Softmax Pro 4.7.1 software. ELISA end point titers were defined as the highest reciprocal serum dilution that yielded absorbance>2-fold background.

TZM.b1 Neutralization Assay

NAb responses against tier 1 and tier 2 HIV-1 pseudoviruses were measured using a luciferase-based assay in TZM.b1 cells as previously (Li et al., Supra; Montefiori et al., Supra). This assay measured the reduction in luciferase reporter gene expression in TZM-b1 cells following a single round of virus infection. The $IC_{50}$ was calculated as the concentration that caused a 50% reduction in relative luminescence units compared with the virus control wells after the subtraction of cell control relative luminescence units. Briefly, 3-fold serial dilutions of serum samples were performed in triplicate (96-well flat bottom plate) in 10% DMEM growth medium (100 μl/well). 200 TCID50 of virus was added to each well in a volume of 50 μl and the plates were incubated for 1 hour at 37° C. TZM.b1 cells were then added ($1\times10^4$/well in 100 μl volume) in 10% DMEM growth medium containing DEAE-Dextran (Sigma) at a final concentration of 11 μg/ml. Murine leukemia virus (MuLV) negative controls were included in all assays to rule out non-specific inhibition. Confirmatory assays were performed utilizing IgG purified by immobilized protein A columns (Pierce). To test variable loop peptide reactivity, purified IgG samples was incubated with V1, V2, or V3 linear peptides for 1 hour at 37° C. prior to addition of pseudovirus. A negative control scrambled 92UG037 V3 peptide was also included in these assays. Viruses in the tier 1 panel were: MW965.26 (clade C), DJ123.8 (clade A), SF162.LS (clade B), BaL.26 (clade B), 92UG037.8 (clade A) and CZA97.012 (clade C). Viruses in the tier 2 clade A panel were: Q769.d22, Q168.a2, Q842.d12, 3718.v3, 0330.v4 and 0439.v5. Viruses in the tier 2 clade B panel were: WIT04160.33, AC10.0.29, REJ0451, 6535.3, SC422661 and TRO.11. Viruses in the tier 2 clade C panel were: ZM109F.PB4, ZM249M, CAP45.2, Du123.6, Du422.1, and ZM197M.

Gene Structure and Cloning Enzymes

Figure 12A:
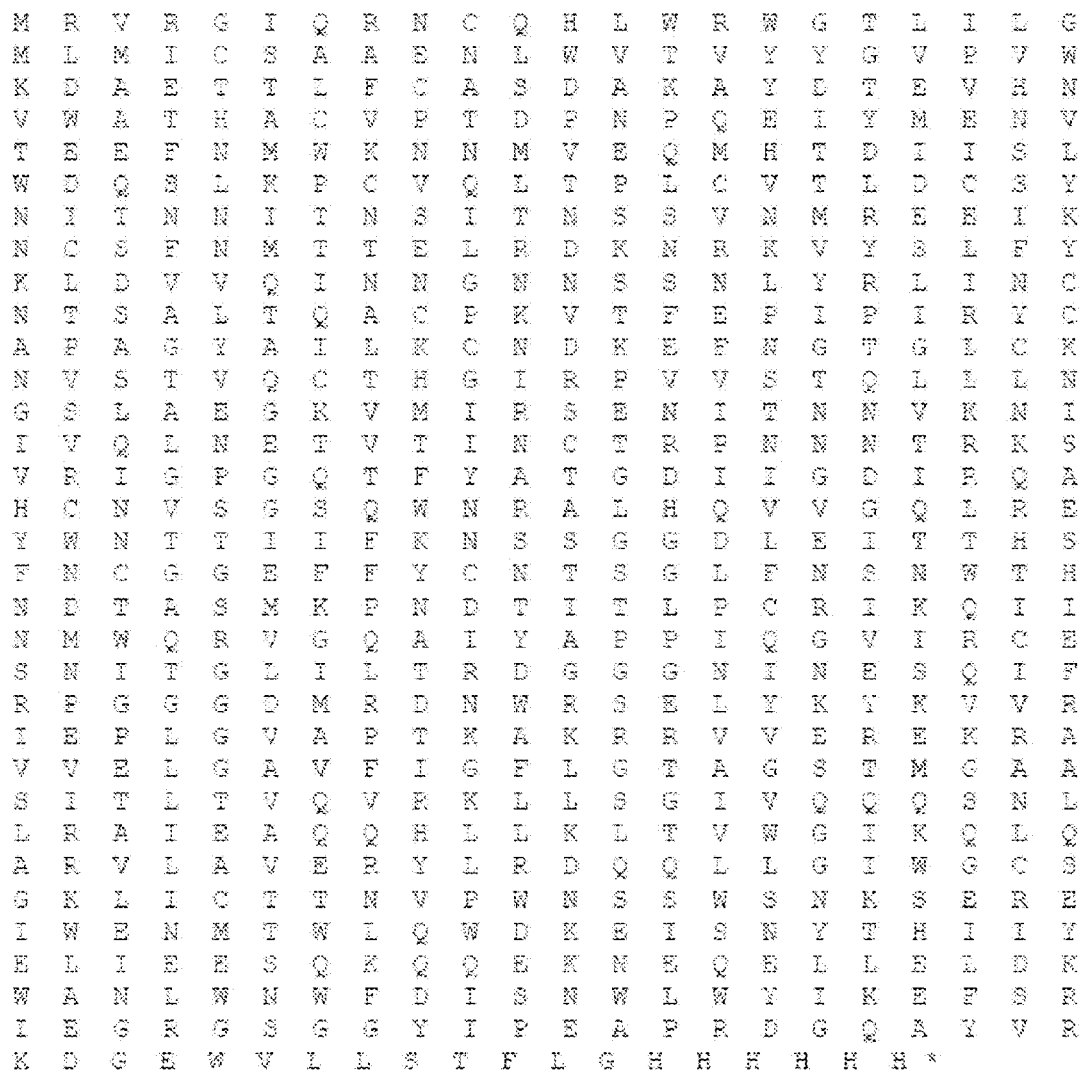
Figure 12B:
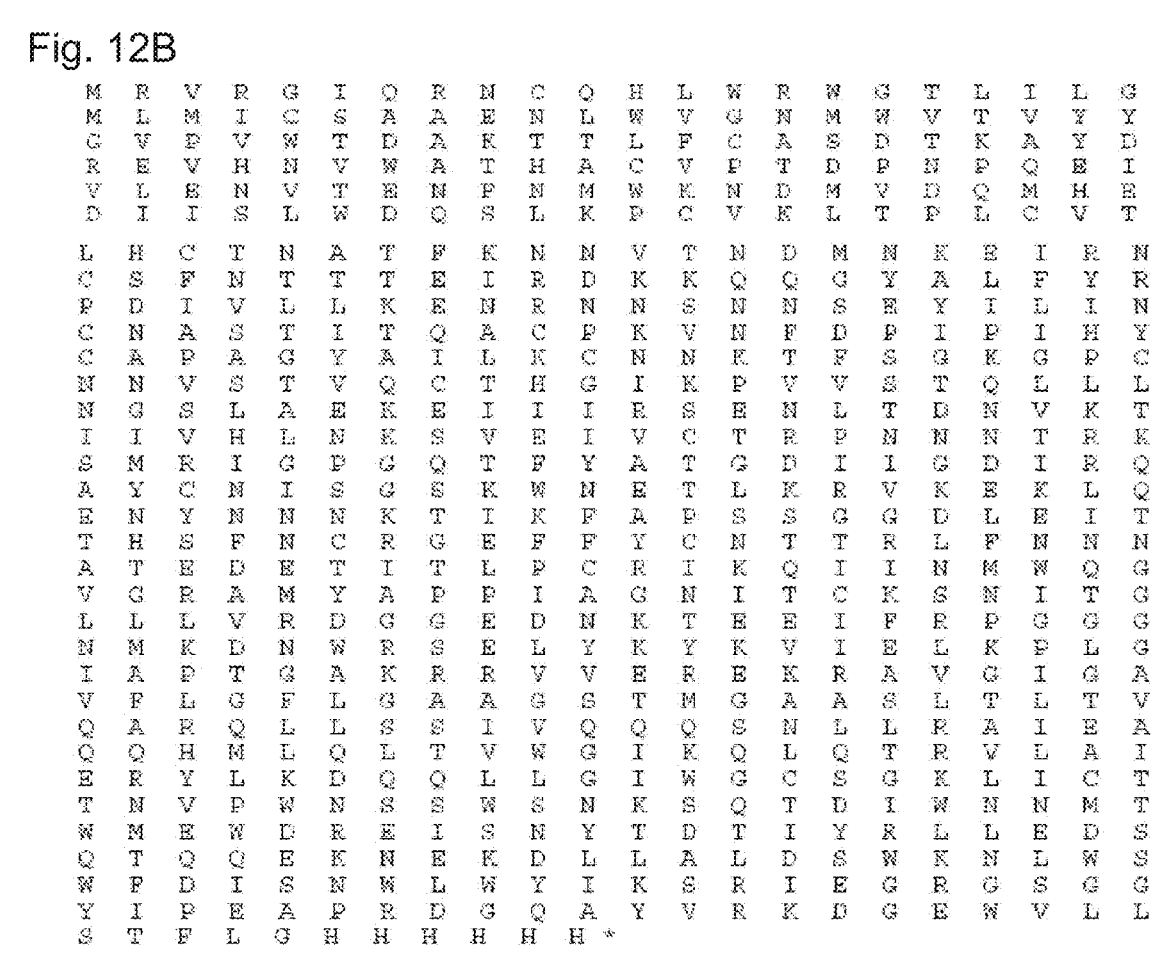

5' unique cloning enzyme: SaD; Kozak sequence: GCCACC; 3' unique cloning enzyme: BamHI; Gene structure: Sali-GCCACC-ATG..Stop-BamHI; Optimize: YES. The 92UG037 gp140-6× His trimer (MCONS leader) amino acid sequence is depicted in FIG. 12A. The CZA97.012 gp140-6× His trimer (MCONS leader) amino acid sequence is depicted in FIG. 12B.

REFERENCES

Beddows et al. (2007) *Virology* 360:329
Li et al. (2006) *J Virol.* 80:1414
Bower et al. (2006) *Vaccine* 24:5442
Kim et al. (2005) *AIDS Res. Hum. Retroviruses* 21:58
Frey et al. (2008) *Proc. Natl. Acad. Sci. USA* 105:3739
Barouch (2008) *Nature* 455:613
Beddows et al. (2007) *Virology* 360:329
Berger et al. (1999) *Annu. Rev. Immunol.* 17:657
Berman et al. (2002) *Aids* 8:591
Binley et al. (2000) *J Virol.* 74:627
Bower et al. (2006) *Vaccine* 24:5442
Burton et al. (2004) *Nat. Immunol.* 5:233
Carrow et al., (1991) *AIDS Res. Hum. Retroviruses* 7:831
Crooks et al. (2007) *Virology* 366:245
Derby et al. (2007) *Virology* 366:433
Dey et al. (2007) *J Virol.* 81:5579
Flynn et al. (2005) *J Infect. Dis.* 191:654
Gallo et al. (2003) *Biochim. Biophys. Acta* 1614:36
Kim et al. (2005) *AIDS Res. Hum. Retroviruses* 21:58
Li et al. (2006) *J Virol.* 80:1414
Montefiori et al. (2007) *PLoS Med.* 4:e348
Momer et al. (2009) *J Virol.* 83:540
Nara et al. (1988) *J Virol.* 62:2622
Page et al. (1991) *Vaccine* 9:47
Pantophle and Burton (2006) *Annu. Rev. Immunol.* 24:739
Pitisuttithum et al. (2006) *J Infect. Dis.* 194:1661
Scheid et al. (2009) *Nature* 458:636
Vogel et al. (1994) *J Immunol.* 153:1895
Walker et al. (2009) *Science* 326:285
Wyatt et al. (1998) *Nature* 393:705
Zhang et al. (2001) *J Biol. Chem.* 276:39577
Zolla-Pazner et al. (2008) *Virology* 372:233.

What is claimed:

1. An isolated nucleic acid molecule encoding at least one gp140 polypeptide, wherein said gp140 polypeptide comprises an amino acid sequence at least 98% identical to residues 30-708 of SEQ ID NO:2, and wherein said gp140 polypeptide comprises an oligomerization domain.

2. An isolated nucleic acid molecule encoding at least one gp140 polypeptide, wherein said gp140 polypeptide comprises an amino acid sequence at least 98% identical to SEQ ID NO:2, and wherein said gp140 polypeptide comprises an oligomerization domain.

3. The isolated nucleic acid molecule of claim 1, wherein said amino acid sequence comprises SEQ ID NO:8.

4. The isolated nucleic acid molecule of claim 1, wherein said amino acid sequence comprises SEQ ID NO:6.

5. The isolated nucleic acid molecule of claim 3, wherein said amino acid sequence comprises SEQ ID NO:6.

6. The isolated nucleic acid molecule of claim 1, wherein said oligomerization domain is a T4 fibritin trimerization domain.

7. A vector comprising the isolated nucleic acid molecule of claim 1.

8. The vector of claim 7, wherein said vector is a plasmid.

9. The vector of claim 7, further comprising a promoter that drives expression of said gp140 polypeptide.

10. A method of recombinantly producing a gp140 polypeptide, said method comprising the steps of:
 (a) contacting a cell with the vector of claim 7;
 (b) expressing said at least one gp140 polypeptide; and
 (c) purifying said gp140 polypeptide.

11. The method of claim 10, wherein the expressed gp140 polypeptide forms a stabilized trimer.

12. The method of claim 10, wherein said cell is a bacterial cell, a yeast cell, an insect cell, or a mammalian cell.

13. The method of claim 12, wherein said cell is a mammalian cell.

14. A pharmaceutical composition comprising the recombinantly produced gp140 polypeptide of claim 10 and a pharmaceutically acceptable carrier, excipient, or diluent.

15. The isolated nucleic acid molecule of claim 2, wherein said oligomerization domain is a T4 fibritin trimerization domain.

16. A vector comprising the isolated nucleic acid molecule of claim 2.

17. A vector comprising the isolated nucleic acid molecule of claim 6.

18. A vector comprising the isolated nucleic acid molecule of claim 15.

19. A method of recombinantly producing a gp140 polypeptide, said method comprising the steps of:
(a) contacting a cell with the vector of claim 18;
(b) expressing said at least one gp140 polypeptide; and
(c) purifying said gp140 polypeptide.

20. A pharmaceutical composition comprising the recombinantly produced gp140 polypeptide of claim 19 and a pharmaceutically acceptable carrier, excipient, or diluent.

21. The isolated nucleic acid molecule of claim 2, wherein said gp140 polypeptide comprises the amino acid sequence of SEQ ID NO:2.

22. The method of claim 19, wherein the expressed gp140 polypeptide forms a stabilized trimer.

* * * * *